(12) United States Patent
Matje et al.

(10) Patent No.: US 10,392,650 B2
(45) Date of Patent: *Aug. 27, 2019

(54) RAPID, LOW-SAMPLE-VOLUME CHOLESTEROL AND TRIGLYCERIDE ASSAYS

(71) Applicant: Theranos IP Company, LLC, Healdsburg, CA (US)

(72) Inventors: Douglas Matje, East Palo Alto, CA (US); Ian Gibbons; Paul Patel, Sunnyvale, CA (US); Elizabeth A. Holmes, San Francisco, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/364,762

(22) Filed: Nov. 30, 2016

(65) Prior Publication Data

US 2017/0175168 A1 Jun. 22, 2017

Related U.S. Application Data

(60) Continuation of application No. 14/604,538, filed on Jan. 23, 2015, now Pat. No. 9,546,394, which is a division of application No. 14/100,870, filed on Dec. 9, 2013, now Pat. No. 9,051,599.

(60) Provisional application No. 61/735,424, filed on Dec. 10, 2012.

(51) Int. Cl.
| | |
|---|---|
| *C12Q 1/60* | (2006.01) |
| *C12Q 1/61* | (2006.01) |
| *G01N 33/92* | (2006.01) |
| *C12Q 1/26* | (2006.01) |
| *C12Q 1/44* | (2006.01) |

(52) U.S. Cl.
CPC .................. *C12Q 1/60* (2013.01); *C12Q 1/26* (2013.01); *C12Q 1/44* (2013.01); *C12Q 1/61* (2013.01); *G01N 33/92* (2013.01); *C12Q 2326/00* (2013.01); *C12Q 2326/90* (2013.01); *C12Q 2326/96* (2013.01); *C12Q 2523/115* (2013.01); *G01N 2333/904* (2013.01); *G01N 2333/908* (2013.01); *G01N 2333/92* (2013.01)

(58) Field of Classification Search
CPC .......................................................... C12Q 1/60
See application file for complete search history.

(56) References Cited

U.S. PATENT DOCUMENTS

| | | | |
|---|---|---|---|
| 4,495,293 A | 1/1985 | Shaffar | |
| 4,544,630 A | 10/1985 | Ziegenhorn et al. | |
| 4,892,815 A | 1/1990 | Kerscher et al. | |
| 5,215,886 A | 6/1993 | Patel et al. | |
| 5,814,472 A | 9/1998 | Miki et al. | |
| 5,888,755 A * | 3/1999 | Miyauchi | C12Q 1/60 435/10 |
| 8,163,472 B2 | 4/2012 | Inomata | |
| 9,051,599 B2 | 6/2015 | Matje et al. | |
| 2008/0318258 A1 | 12/2008 | Ogihara et al. | |
| 2016/0024554 A1 | 1/2016 | Matje et al. | |

FOREIGN PATENT DOCUMENTS

| | | |
|---|---|---|
| EP | 0230786 A1 | 8/1987 |
| EP | 1577398 A1 | 9/2005 |
| EP | 1739189 A1 | 1/2007 |
| EP | 1930443 A1 | 6/2008 |
| EP | 2105739 B1 | 2/2013 |

OTHER PUBLICATIONS

Friedewald WT et al. Estimation of the concentration of low-density lipoprotein cholesterol in plasma, without the use of the preparative centrifuge, Clinical Chemistry 18:499-502 (1972).
Kimberly M.M. et al. Selection, validation, standardization, and performance of a designated comparison method for HDL-cholesterol for use in the cholesterol reference method laboratory network. Clinical Chemistry, Oct. 1999;45(10):1803-1812, especially abstract, p. 1804.
Nauck et al. Methods for measurement of LDL-cholesterol: a critical assessment of direct measurement by homogeneous assays versus calculation, Clinical Chemistry, American Association for Clinical Chemistry, Washington, DC, vol. 48, No. 2, Jan. 1, 2002, pp. 236-254.
Notice of Allowance dated Dec. 19, 2014 for U.S. Appl. No. 14/100,870.
Notice of Allowance dated Sep. 7, 2016 for U.S. Appl. No. 14/604,538.
Office Action dated Feb. 4, 2016 for U.S. Appl. No. 14/604,538.
Office Action dated Jun. 21, 2016 for U.S. Appl. No. 14/604,538.
Sampson et al. "Triple lipid screening test: a homogenous sequential assay for HDL-cholesterol, total cholesterol, and triglycerides", Clinical Chemistry, 2001. 47(3):532-539.

(Continued)

Primary Examiner — Bin Shen

(57) ABSTRACT

Reagents, assays, methods, kits, devices, and systems for rapid measurement of cholesterol and cholesterol sub-fractions from a blood sample are provided. Total cholesterol, low density lipoprotein cholesterol, and high density lipoprotein cholesterol can be measured in a single assay using kinetic measurements, under conditions in which cholesterol sub-species are converted to a detectable product at distinct rates. The detectable product is measured at different times after assay initiation. A lipase, cholesterol esterase, cholesterol oxidase and a peroxidase may be used together to produce colored product in amounts directly proportional to the quantity of cholesterol converted. Methods for calculating very-low density lipoprotein cholesterol levels by further including triglyceride measurements are disclosed. Assays may be performed in a single reaction mixture, allowing more accurate and precise cholesterol determinations, including ratios of cholesterol sub-fractions to total cholesterol, at less expense, than would be expected by performing several different assays in different reaction mixtures.

10 Claims, 5 Drawing Sheets

(56) References Cited

OTHER PUBLICATIONS

Sampson et al. Dual HDL/total Cholesterol Test: A Single-Tube, Homogeneous Assay for Sequential Measurement of HDL Cholesterol and Total Cholesterol, Annals of Clinical Biochemistry., vol. 37, No. 4, Jul. 1, 2000, pp. 479-487.

Siemens Healthcare Diagnostics Inc. LDL Cholesterol Direct (DLDL), Advia® Chemistry Systems Instructions for Use Feb. 2011.

Sniderman AD et al. Triglycerides and small dense LDL: the twin Achilles heels of the Friedewald formula, Clinical Biochemistry 36:499-504 (2003).

The International Search Report and the Written Opinion dated May 15, 2014 for Application No. PCT/US2013/074211.

Warnick GR et al. Evolution of Methods for Measurement of HDL-Cholesterol: From Ultracentrifugation to Homogeneous Assays, Clinical Chemistry 47(9):1579-1596 (2001).

\* cited by examiner

GK = Glycerol Kinase

GPO = Glycerol-3-phosphate Oxidase

HRP = Horse Radish Peroxidase

ALPS = N-Ethyl-N-(3-sulfopropyl) aniline

RAPID, LOW-SAMPLE-VOLUME CHOLESTEROL AND TRIGLYCERIDE ASSAYS

CROSS-REFERENCE TO RELATED APPLICATIONS

This application is a continuation of, claims priority to, and the benefit under 35 U.S.C. § 120 of, U.S. patent application Ser. No. 14/604,538, now U.S. Pat. No. 9,546,394, which is a divisional of, claims priority to, and the benefit under 35 U.S.C. § 120 of, U.S. patent application Ser. No. 14/100,870 filed on Dec. 9, 2013, now U.S. Pat. No. 9,051,599, which application claims priority to, and the benefit under 35 U.S.C. § 119 of, U.S. Provisional Patent Application 61/735,424 filed on Dec. 10, 2012, the disclosures of all of which applications are hereby incorporated by reference in their entireties.

BACKGROUND

Lipids, and in particular cholesterol, play a vital role in human health and disease. Cholesterol is an essential nutrient and a critical component of lipid membranes which form the boundaries surrounding cells and cellular organelles.

Excessive cholesterol, however, is very dangerous in that it can accumulate as "plaques" in blood vessels and can cause thrombosis, stroke and other potentially lethal consequences in humans. To mitigate these risks, lipids, especially cholesterol, are packaged into lipoproteins for transport through the body in blood.

Various heterogeneous forms of lipoproteins containing cholesterol (C) and triglycerides (TG) are known, including, for example, chylomicrons, very low density lipoprotein (VLDL), low density lipoprotein (LDL), and high density lipoprotein (HDL). The cholesterol content of these lipoproteins is termed VLDL-cholesterol (VLDL-C), LDL-cholesterol (LDL-C), and HDL-cholesterol (HDL-C), respectively.

Measurements or derived values of the cholesterol content of VLDL, LDL, HDL and the total cholesterol (TC) content of blood plasma or serum are routinely made to assess the risk of atherosclerosis and the beneficial effects of "cholesterol-lowering" drugs such as "statins".

In prior art methods, centrifugation of blood samples provides distinguishable VLDL, LDL and HDL fractions in blood serum or plasma; these fractions form distinct bands which move at different rates under the centrifugal force because of their differing densities. Lipoproteins also can be separated by precipitation by use of differential precipitation using reagents such as dextran-sulfates, cyclodextrin-sulfates, and cations. For example, VLDL and LDL can be completely precipitated while leaving all the HDL in solution. Once VLDL and LDL have been removed by centrifugation or filtration, the remaining cholesterol is associated only with the HDL fraction. Other prior art methods may be used to estimate HDL-C and LDL-C which employ enzymes that are modified, for example, by covalently attaching polyethylene glycol (PEG) chains. The PEG is believed to restrict enzyme activity to specific lipoprotein fractions. These prior art methods may also use specific reagents which selectively solubilize or shield specific lipoprotein fractions so that only a single lipoprotein fraction is precipitated or may react with assay chemistry in an assay.

In order for these cholesterol-content measurements to be valid, it is essential that they be very accurate and precise (error less than 5%) since small differences are clinically significant. Conventional means for measurement of cholesterol sub-fractions involve several independent assays (typically at least three, TC, LDL-C, and HDL-C) and/or measurement of three analytes (TC, TG, HDL-C) plus a calculated value for LDL-C using the Friedewald formula:

$$HDL\text{-}C \approx TC - LDL\text{-}C - k \times TG$$

Where "TG" is the triglyceride level, "×" indicates multiplication, and "k" is 0.2 for quantities measured in mg/dl (k is about 0.45 if the quantities are measured in mmol/l).

The Friedewald formula may be equivalently expressed in terms of LDL-C as follows:

$$LDL\text{-}C \approx TC - HDL\text{-}C - k \times TG$$

Where again "TG" is the triglyceride level, "×" indicates multiplication, and "k" is 0.2 for quantities measured in mg/dl (k is about 0.45 if the quantities are measured in mmol/l).

Of critical importance are the relative levels of the sub-forms of lipoprotein cholesterol: for example, the ratio of HDL-C to TC (HDL-C/TC), the ratio of LDL-C to TC (LDL-C/TC), or the ratio of VLDL-C to TC (VLDL-C/TC). The levels of the sub-forms of lipoprotein cholesterol are typically measured separately or by expensive and cumbersome physical separation methods such as centrifugation or electrophoresis. Since these levels are conventionally measured in several independent assays each with its own sources of error, the cumulative error in the computed ratios of cholesterol sub-fractions will be greater than that desired for effective diagnosis and monitoring of therapy. Additionally, the costs of analysis of lipoprotein cholesterol sub-fractions are increased by the need for several assays.

INCORPORATION BY REFERENCE

All patents, patent applications, and publications mentioned herein are hereby incorporated by reference in their entireties.

SUMMARY

Applicants have found that very accurate and precise values for T-C, LDL-C and HDL-C can be obtained in a single assay for lipoprotein cholesterol using kinetic measurements, without need for precipitation of lipoproteins and without separation steps. Assays as disclosed herein use a lipase (e.g., a cholesterol esterase), an oxidase (e.g., a cholesterol oxidase) and a peroxidase to form a colored product. Assays as disclosed herein may use a lipase (e.g., a cholesterol esterase), a dehydrogenase (e.g., a cholesterol dehydrogenase) and nicotine adenine dinucleotide to form a light-absorbing product (e.g., NADH) or other detectable product. Such products may be measurable by spectrophotometry. In the assays disclosed herein, the amount of product formed from all the cholesterol-containing lipoprotein species is directly proportional to the quantity of cholesterol converted. The assays, methods, reagents, and kits disclosed herein are useful for rapid, efficient, and inexpensive assays of lipoprotein cholesterol and lipoprotein cholesterol sub-fractions, and advantageously provide for measurements of lipoprotein cholesterol and lipoprotein cholesterol sub-fractions in a single assay. Assays disclosed herein advantageously provide for measurements of lipoprotein cholesterol and lipoprotein cholesterol sub-fractions without need for lipoprotein precipitation. Assays disclosed herein advantageously provide for measurements of lipoprotein cholesterol and lipoprotein cholesterol sub-fractions without the need for centrifugation or for electrophoresis.

Applicants have found that it is possible to provide assay conditions (e.g., reagents, protocol and temperature) so that the kinetics of reactions converting HDL-C, LDL-C and VLDL-C to colored product proceed at significantly different rates, while still allowing essentially complete reaction of all lipoprotein species (e.g., HDL, LDL, and VLDL) by the end of the assay. For example, in assays disclosed herein the time course for HDL-C has a half-time estimated at less than one minute whereas the LDL-C conversion has a lag phase and an overall sigmoid shape centered on about three minutes. In assays disclosed herein, the remaining lipoprotein cholesterol (chylomicrons and VLDL-C) react even more slowly (half-time of about five minutes or longer). These differences in half-time and reaction kinetics between different cholesterol species enable the de-convolution of an assay signal to that attributable to each species using a simple algorithm even though, for example, signal is being produced from more than one species during certain times during the assay. Accordingly, reagent formulations for use in the assays and methods disclosed herein are designed to achieve the kinetic differentiation of lipoprotein species HDL, LDL, and VLDL in a single assay.

The novel methods and assays disclosed herein make use of Applicants' surprising finding that in these assays cholesterol sub-species are converted to the measured product at distinct rates. Accordingly, HDL-C is converted very rapidly to product, while LDL-C is converted to product more slowly than HDL-C is converted to product and VLDL-C and chylomicron cholesterol are converted even more slowly. Complete conversion of total cholesterol to product is even slower than the conversion of HDL-C or LDL-C to product. Such differences in rates of conversion to product allow the measurement of cholesterol from different lipoprotein species to be made in a single solution at different times, thus reducing the number of steps needed for such measurements, reducing possible errors and simplifying the procedures.

Accordingly, Applicants disclose herein methods of determining HDL-C, LDL-C and TC in a single sample, or portion of a sample, of blood. These methods allow determination of HDL-C, LDL-C and TC in a single sample, or portion of a sample, of blood without substantial precipitation of lipoproteins, e.g., without substantial precipitation of HDL or LDL in the sample, or portion of a sample, of blood during the determination. As disclosed herein, the amount of HDL-C in a blood sample may be measured without substantial lipoprotein precipitation by colorimetric determination of the amount of peroxide formed in a first period of time following combination of reagents effective to allow oxidation of cholesterol released from lipoproteins in the sample. The first period of time may be, for example, a period of time that is less than about 3 minutes, and in embodiments may be a period of time of about 2 minutes. As disclosed herein, the amount of LDL-C in a blood sample may be measured without substantial lipoprotein precipitation by colorimetric determination of the amount of peroxide formed in a second period of time following combination of reagents effective to allow oxidation of cholesterol released from lipoproteins in the sample. In embodiments, the amount of LDL-C in a blood sample may be measured by the difference between colorimetric determinations made at the beginning of said second period of time and colorimetric determinations made at the end of said second period of time. The second period of time may be, for example, a period of time that is between about 2 minutes and about 6 minutes following combination of reagents effective to allow oxidation of cholesterol released from lipoproteins in the sample. As disclosed herein, the amount of TC in a blood sample may be measured without substantial lipoprotein precipitation by colorimetric determination of the amount of peroxide formed following combination of reagents effective to allow oxidation of cholesterol released from lipoproteins in the sample. This TC measurement (e.g., colorimetric determination) may be made at a time at the beginning of, or at any particular time during, a third period of time. The third period of time comprises a period of time after said second period of time, and may be, for example, a period of time that begins about 6 minutes following combination of reagents effective to allow oxidation of cholesterol released from lipoproteins in the sample. For consistency of measurement between different samples, where different samples are measured in different determinations, the colorimetric determination for each different sample may be made at the same time after the beginning of said third period of time for each sample.

Accordingly, HDL-C, LDL-C, and TC measurements may be made in a single sample, or a single portion of a sample, of blood of a subject. In embodiments, as disclosed herein, HDL-C, LDL-C, and TC measurements may be made sequentially in a single sample, or a single portion of a sample, of blood of a subject. For example, from these measurements, the level of VLDL-C in a single sample, or a single portion of a sample, of blood of a subject may be calculated by the relation VLDL-C=TC−(HDL-C+LDL-C), or by other relationships. In embodiments, the level of VLDL-C in a single sample, or a single portion of a sample, of blood of a subject may be calculated from these measurements, for example, by a relation of the form VLDL-C=$\alpha$TC+$\beta$HDL-C+$\gamma$LDL-C+$\lambda$, where $\alpha$, $\beta$, and $\gamma$ are constants which multiply TC, HDL-C, and LDL-C, respectively; and where $\lambda$ is an additive constants to be added to the sum of all other factors, respectively. In yet further embodiments, the level of VLDL-C in a single sample, or a single portion of a sample, of blood of a subject may be calculated from other relationships using some or all of the measured values of TC, HDL-C, and LDL-C and multiplicative and additive constants similar in form to the relationships provided above.

Applicants thus disclose herein novel and useful measurements of HDL-C, LDL-C, and TC, and calculation of VLDL-C, which may be made on a single blood sample, or portion of blood sample, reducing the amount of blood needed for such measurements, reducing the complexity of the methods needed to measure these different lipoprotein fractions in blood, and providing accurate and rapid blood lipoprotein measurements. These measurements may be made without substantial precipitation of lipoproteins in the sample.

Applicants also disclose herein methods for determining triglyceride levels in blood samples, where the level (equivalently: amount) of triglyceride (TG) may be determined by methods in which a sample of blood is contacted with a lipase, a kinase, and an oxidase to free glycerol from TG in the blood sample, to phosphorylate the glycerol, and then to provide hydrogen peroxide. The hydrogen peroxide, in the presence of a peroxidase forms a colorant, the measurement of which provides a determination of the TG level in the blood sample.

Applicants disclose herein novel and useful measurements of HDL-C, LDL-C, TC, and TG which provide accurate and rapid blood lipoprotein measurements. The measurements of HDL-C, LDL-C and TC may be made on one sample or portion of sample of blood, while the TG measurements may be made on a different sample or portion of sample of blood. These measurements may be made without substantial precipitation of lipoproteins in the samples. Together, these measurements of four blood lipid components are made on only two samples, or two portions of a sample or samples, of blood from a subject. Applicants disclose herein further, improved methods for calculating VLDL-C in the blood of a subject, using HDL-C, TC, and TG measurements or using HDL-C, LDL-C, TC, and TG measurements. In embodiments, VLDL-C may be calculated from HDL-C, TC, and TG measurements, or from HDL-C, LDL-C, TC, and TG measurements, where these measurements are made according to the methods disclosed herein. In embodiments, the level of VLDL-C in a single sample, or a single portion of a sample, of blood of a subject may be calculated from these measurements, for example, by a relation of the form VLDL-C=$\alpha$TC+$\beta$HDL-C+$\gamma$LDL-C+$\delta$TG+$a_1$(TG+$\epsilon$)(TC+$\kappa$)+$\lambda$, where $\alpha$, $\beta$, $\gamma$, $\delta$, and $a_1$ are constants which multiply TC, HDL-C, LDL-C, TG, and (TG+$\epsilon$)(TC+$\kappa$), respectively; and where $\epsilon$, $\kappa$, and $\lambda$ are additive constants to be added to TG, TC, and the sum of all other factors, respectively. In further embodiments, the level of VLDL-C in a single sample, or a single portion of a sample, of blood of a subject may be calculated from these measurements, for example, by a relation of the form VLDL-C=$\alpha$TC+$\beta$HDL-C+$\delta$TG+$a_1$(TG+$\epsilon$)(TC+$\kappa$)+$\lambda$, where $\alpha$, $\beta$, $\delta$, and $a_1$ are constants which multiply TC, HDL-C, TG, and (TG+$\epsilon$)(TC+$\kappa$), respectively; and where $\epsilon$, $\kappa$, and $\lambda$ are additive constants to be added to TG, TC, and the sum of all other factors, respectively. In yet further embodiments, the level of VLDL-C in a single sample, or a single portion of a sample, of blood of a subject may be calculated from other relationships using some or all of the measured values of TC, TG, HDL-C, and LDL-C and multiplicative and additive constants similar in form to the relationships provided above.

In embodiments, reagent formulations for use in the assays and methods disclosed herein are designed to achieve the kinetic differentiation described above without precipitation of lipoproteins. In reagents and assays disclosed herein, formation of complexes of lipoproteins with cations (optionally divalent cations such as magnesium, calcium, manganese, cobalt, cadmium, or other cations) and a negatively charged polysaccharide (such as, e.g., a dextran ester such as dextran-sulfate, a cyclodextrin ester such as $\alpha$-cyclodextrin-sulfate, heparin, or other negatively charged polysaccharide) is achieved in conditions where no precipitation of lipoproteins occurs. For example, in embodiments, lipoprotein complex formation with magnesium ions and dextran sulfate is achieved in conditions where little or no precipitation of lipoproteins occurs. Amphiphilic compounds, such as surfactants may be included in reagents and assays disclosed herein. For example, a variety of surfactants are suitable for use in keeping the lipoproteins soluble. In embodiments, the reagents provide ingredients effective to modify the LDL and VLDL lipoprotein particle surfaces in such a way as to restrict but not prevent access (e.g., by cholesterol esterases and/or oxidases) to LDL and VLDL cholesterol and cholesterol esters. The use of reagents and methods suitable for such modification of LDL and VLDL particle surfaces is effective to slow the formation of colored product from these lipoprotein species as compared to the rate of formation of colored product in similar assays performed without the interactants and surfactants, or with such agents at different concentrations and relative proportions than are found in the assays and reagents disclosed herein. Slowing of the formation of colored product from lipoprotein species may be useful in order to provide separation of reaction kinetics effective to enable the measurement of cholesterol content of different lipoprotein fractions at different times without need for physical separation of the different lipoprotein fractions (e.g., without need for centrifugation or electrophoresis).

Accordingly, Applicants disclose herein a first reagent for use in an assay for the simultaneous, rapid measurement of at least two of total cholesterol (TC), LDL-cholesterol (LDL-C) and HDL-cholesterol (HDL-C) in a sample of blood from a subject without substantial precipitation of said blood lipoproteins, comprising a lipoprotein solubilization agent and a lipoprotein interactant. In embodiments, a first reagent may comprise a buffer. In embodiments, a lipoprotein solubilization agent for use in a first reagent as disclosed herein may comprise a surfactant. A lipoprotein interactant may comprise, for example, a cyclodextrin, a dextran, or both. In embodiments, a lipoprotein interactant for use in such a first reagent may comprise a low molecular weight dextran. In embodiments, a lipoprotein interactant for use in such a first reagent may comprise an $\alpha$-cyclodextrin. In embodiments, a first reagent may comprise a colorant. In embodiments, a first reagent may include one or both of an aniline-containing compound and an aminoantipyrene compound, effective that both compounds, in the presence of peroxide and a peroxidase, react to form a detectable product. In embodiments of the reagents, assays, methods, and kits disclosed herein, such a first reagent may comprise $\alpha$-cyclodextrin sulfate, dextran sulfate, magnesium chloride, 4 aminoantipyrene and a buffer, such as a phosphate buffer. In embodiments of the reagents, assays, methods, and kits disclosed herein, such a first reagent may comprise $\alpha$-cyclodextrin sulfate (1 mM), dextran sulfate (20 μM), magnesium chloride (4 mM), 4 aminoantipyrene (2.25 mM) and $Na_xPO_4$ (100 mM) (where $Na_xPO_4$ is a sodium phosphate salt; e.g., may be $NaH_2PO_4$, $Na_2HPO_4$, or $Na_3PO_4$). In embodiments, the pH of such a first reagent may be between about pH 5 and about pH 9, or between about pH 6 and about pH 8, optionally between about pH 6.8 and about pH 7.8, e.g., about pH 7.4.

Applicants also disclose a second reagent for use in an assay for the simultaneous, rapid measurement of at least two of total cholesterol (TC), LDL-cholesterol (LDL-C) and HDL-cholesterol (HDL-C) in a sample of blood from a subject without substantial precipitation of said blood lipoproteins, said second reagent comprising a lipase, an oxidase, and a colorant. In embodiments, a second reagent may comprise a buffer. In embodiments of said second reagent, a lipase may comprise a cholesterol esterase, an oxidase may comprise a cholesterol oxidase, and a colorant may comprise a peroxidase, a substrate for a peroxidase, or both. In embodiments, both a peroxidase and a substrate for a peroxidase are present in said second reagent.

In embodiments, said second reagent may comprise a buffer, an amphiphilic agent, a cholesterol esterase, a cholesterol oxidase, and a colorant. In embodiments, an amphiphilic agent for use in such a second reagent may comprise a surfactant. In embodiments, a colorant for use in such a second reagent may comprise a peroxidase and a substrate for a peroxidase. In embodiments, a colorant for use in such a second reagent may comprise horseradish peroxidase. In embodiments, a colorant for use in such a second reagent may comprise an aniline-containing compound, such as N-Ethyl-N-(2-hydroxy-3-sulfopropyl)-3,5-dimethoxyaniline (ALPS), may comprise an aminoantipyrene compound, such as 4-aminoantipyrene, or other compounds and combinations of compounds which react with an enzyme such as a peroxidase (e.g., horseradish peroxidase). In embodiments, a second reagent may include both an aniline-containing compound and an aminoantipyrene compound, effective that both compounds, in the presence of peroxide and a peroxidase, react to form a detectable product. In embodiments, a lipase may comprise a cholesterol esterase. In embodiments, a cholesterol esterase for use in such a second reagent may comprise a bacterial cholesterol esterase, such as, for example, a cholesterol esterase from a *Pseudomonas* bacterium. In embodiments, an oxidase may comprise a cholesterol oxidase. In embodiments, a cholesterol oxidase for use in a second reagent as disclosed herein may comprise a bacterial cholesterol oxidase, such as a cholesterol oxidase from a *Pseudomonas* bacterium. In embodiments of the reagents, assays, methods, and kits disclosed herein, such a second reagent may comprise a buffer, such as a phosphate buffer (e.g., $Na_xPO_4$ (where $Na_xPO_4$ is a sodium phosphate salt; e.g., may be $NaH_2PO_4$, $Na_2HPO_4$, or $Na_3PO_4$)), Triton X-100, pluronic L64, N-Ethyl-N-(2-hydroxy-3-sulfopropyl)-3,5-dimethoxyaniline (ALPS), a *Pseudomonas* cholesterol esterase, and a *Pseudomonas* cholesterol oxidase. For example, such a second reagent may comprise $Na_xPO_4$ (50 mM), Triton X-100 (0.06%), pluronic L64 (3 g/L), N-Ethyl-N-(2-hydroxy-3-sulfopropyl)-3,5-dimethoxyaniline (ALPS) (3 mM), cholesterol esterase from *Pseudomonas* sp. (750 U/L), and cholesterol oxidase from *Pseudomonas* sp. (1.5 kU/L). In embodiments, the pH of such a second reagent may be between about pH 5 and about pH 9, or between about pH 6 and about pH 8, optionally between about pH 6.8 and about pH 7.8, e.g., about pH 7.4.

Applicants disclose herein methods and reagents for use in a cholesterol assay, including second reagents comprising a lipase, an oxidase, and a colorant, said second reagents comprising a lipoprotein interactant at a concentration level that, when used in methods disclosed herein, provides for conversion of HDL-C to a measureable colored product (or product measureable, e.g., in the near ultraviolet range of the spectrum) at a substantially different rate than for conversion of LDL-C to a measureable colored product (or product measureable, e.g., in the near ultraviolet range of the spectrum). Applicants disclose herein methods and reagents for use in a cholesterol assay comprising a lipase, an oxidase, and a colorant, including second reagents comprising a lipoprotein interactant at a concentration level that, when used in methods disclosed herein, provides for conversion of HDL-C to a measureable colored product at a substantially different rate than for conversion of VLDL-C to a measureable colored product. Applicants disclose herein methods and reagents for use in a cholesterol assay comprising a lipase, an oxidase, and a colorant, including second reagents comprising a lipoprotein interactant at a concentration level that, when used in methods disclosed herein, provides for conversion of LDL-C to a measureable colored product at a substantially different rate than for conversion of VLDL-C to a measureable colored product. Applicants disclose herein methods and reagents for use in a cholesterol assay comprising a lipase, an oxidase, and a colorant, including second reagents comprising a lipoprotein interactant at a concentration level that, when used in methods disclosed herein, provides for conversion of HDL-C to a measureable colored product at a substantially different rate than for conversion of LDL-C and/or VLDL-C to a measureable colored product. Applicants disclose herein methods and reagents for use in a cholesterol assay comprising a lipase, an oxidase, and a colorant, including second reagents comprising a lipoprotein interactant at a concentration level that, when used in methods disclosed herein, provide for conversion of LDL-C to a measureable colored product at a substantially different rate than for conversion of HDL-C and VLDL-C to a measureable colored product.

In embodiments, a colorant may comprise a peroxidase and a substrate for a peroxidase. For example, in embodiments, a colorant may comprise a peroxidase, an aniline-containing compound, and an aminoantipyrene compound.

Applicants disclose herein reagents for use in a cholesterol assay comprising a cholesterol esterase and a cholesterol oxidase, including reagents comprising a lipoprotein interactant at a concentration level that provides for conversion of HDL-C to a measureable colored product at a substantially different rate than for conversion of LDL-C and VLDL-C to a measureable colored product, and provides for conversion of HDL-C to a measureable colored product at a substantially different rate than for conversion of LDL-C and VLDL-C to a measureable colored product.

Applicants disclose herein reagents for use in a cholesterol assay comprising a cholesterol esterase and a cholesterol oxidase, including reagents comprising a negatively charged polysaccharide derivative and a divalent cation in concentrations effective that there is no substantial precipitation of LDL, or that there is no substantial VLDL precipitation, or both, when a sample of blood or a portion of a blood sample contacts said reagent. Applicants disclose herein reagents for use in a cholesterol assay comprising a cholesterol esterase and a cholesterol oxidase, said reagents comprising a ratio of negatively charged polysaccharide to divalent cations of between about 0.002 to about 0.02, and in embodiments of about 0.005, effective that there is no substantial precipitation of HDL, or that there is no substantial precipitation of LDL, or that there is no substantial precipitation of VLDL, when a sample of blood or a portion of a blood sample contacts said reagent. In embodiments, said reagent comprises a first reagent as disclosed herein.

Applicants disclose herein reagents for use in a cholesterol assay comprising a cholesterol esterase and a cholesterol oxidase, said reagents comprising a negatively charged polysaccharide, a divalent cation, and surfactant in concentrations effective that there is no substantial precipitation of HDL, or that there is no substantial precipitation of LDL, or that there is no substantial precipitation of VLDL, when a sample of blood or a portion of a blood sample contacts said reagent. In embodiments, said reagent comprises a first reagent as disclosed herein.

Applicants disclose herein reagents for use in a cholesterol assay comprising a cholesterol esterase and a cholesterol oxidase, said reagents comprising dextran sulfate (or other negatively charged polysaccharide) and magnesium (or other divalent cation) in concentrations effective that there is no substantial precipitation of HDL, or that there is no substantial precipitation of LDL, or that there is no substantial precipitation of VLDL, when a sample of blood or a portion of a blood sample contacts said reagent. Applicants disclose herein reagents for use in a cholesterol assay comprising a cholesterol esterase and a cholesterol oxidase, said reagents comprising a ratio of dextran sulfate (or other negatively charged polysaccharide) to magnesium ions (or other divalent cations) of between about 0.002 to about 0.02, and in embodiments of about 0.005, effective that there is no substantial precipitation of HDL, or that there is no substantial precipitation of LDL, or that there is no substantial precipitation of VLDL, when a sample of blood or a portion of a blood sample contacts said reagent or composition. Applicants disclose herein reagents for use in a cholesterol assay comprising a cholesterol esterase and a cholesterol oxidase, said reagents comprising dextran sulfate, magnesium, and surfactant in concentrations effective that there is no substantial precipitation of LDL, or that there is no substantial VLDL precipitation, or both, when a sample of blood or a portion of a blood sample contacts said reagent or composition. In embodiments, said reagent comprises a first reagent as disclosed herein.

Applicants further disclose herein a composition for use in an assay for the simultaneous, rapid measurement of at least two of total cholesterol (TC), LDL-cholesterol (LDL-C) and HDL-cholesterol (HDL-C) in a sample of blood from a subject without substantial precipitation of said blood lipoproteins, comprising a lipoprotein solubilization agent, a lipoprotein interactant, a lipase, an oxidase, and a colorant. In embodiments, such a composition may comprise a buffer. In embodiments, the colorant comprises a peroxidase, an aniline-containing compound, and an aminoantipyrene compound. In embodiments, the composition includes ingredients from the first reagent and the second reagent as disclosed herein. Such a composition may be provided, for example, by combination of said first reagent and said second reagent as disclosed herein. In embodiments, such a composition may comprise a negatively charged polysaccharide and a salt comprising a divalent cation (e.g., a magnesium salt and dextran sulfate), wherein the ratio of negatively charged polysaccharide to divalent cation (e.g., dextran sulfate to magnesium ions) is between about 0.002 to about 0.02, and in embodiments the ratio is about 0.005, effective that there is no substantial precipitation of HDL, or that there is no substantial precipitation of LDL, or that there is no substantial precipitation of VLDL, when a sample of blood or a portion of a blood sample contacts said composition. In embodiments, such a composition comprises said first reagent and said second reagent, or an aliquot of said first reagent and an aliquot of said second reagent. In further embodiments, such a composition comprises said first reagent, said second reagent, and a sample of blood, or an aliquot or aliquots of one or more of said first reagent, said second reagent, and said sample of blood.

In embodiments, a lipoprotein solubilization agent in such a composition may comprise a surfactant. In embodiments, a lipoprotein interactant in such a composition may comprise a divalent cation (e.g., magnesium ion) and a negatively charged polysaccharide derivative. A negatively charged polysaccharide derivative may comprise a cyclodextrin-ester, a dextran-ester, or both a cyclodextrin-ester and a dextran-ester. For example, a dextran-ester may comprise a low molecular weight dextran-ester, e.g., a low molecular weight dextran sulfate, and a cyclodextrin-ester may comprise an α-cyclodextrin-ester, e.g., α-cyclodextrin-sulfate. In embodiments, a lipase may comprise a cholesterol esterase. In embodiments, an oxidase may comprise a cholesterol oxidase. In embodiments, a colorant may comprise a peroxidase.

Accordingly, in embodiments, a composition for use in a cholesterol assay as disclosed herein may comprise a cholesterol esterase; a cholesterol oxidase; a peroxidase; a substrate for a peroxidase; a surfactant; a salt containing a divalent cation; and a negatively charged polysaccharide (e.g., a dextran derivative such as dextran sulfate). In embodiments, a substrate for a peroxidase in such a composition comprises both an aniline-containing compound and an aminoantipyrene compound, effective that both compounds, in the presence of peroxide and a peroxidase, react to form a detectable product. In embodiments, a substrate for a peroxidase may comprise other compounds and combinations of compounds which react with a peroxidase (e.g., horseradish peroxidase). An aniline-containing compound may be, for example, N-Ethyl-N-(2-hydroxy-3-sulfopropyl)-3,5-dimethoxyaniline (ALPS). An aminoantipyrene compound may be 4-aminoantipyrene.

In embodiments, a composition for use in a cholesterol assay as disclosed herein may comprise dextran sulfate (or other negatively charged polysaccharide) and magnesium in concentrations effective that there is no substantial precipitation of HDL, or that there is no substantial precipitation of LDL, or that there is no substantial precipitation of VLDL, when a sample of blood or a portion of a blood sample contacts said composition. Applicants disclose herein compositions for use in a cholesterol assay comprising a cholesterol esterase and a cholesterol oxidase, said compositions comprising a ratio of dextran sulfate to magnesium ions of between about 0.002 to about 0.02, and in embodiments of about 0.005, effective that there is no substantial precipitation of HDL, or that there is no substantial precipitation of LDL, or that there is no substantial precipitation of VLDL, when a sample of blood or a portion of a blood sample contacts said reagent. Applicants disclose herein compositions for use in a cholesterol assay comprising a cholesterol esterase and a cholesterol oxidase, said compositions comprising dextran sulfate, magnesium, and surfactant in concentrations effective that there is no substantial precipitation of LDL, or that there is no substantial VLDL precipitation, or both, when a sample of blood or a portion of a blood sample contacts said composition.

In embodiments, a composition for use in an assay for the simultaneous, rapid measurement of at least two of total cholesterol (TC), LDL-cholesterol (LDL-C) and HDL-cholesterol (HDL-C) in a sample of blood from a subject without substantial precipitation of said blood lipoproteins may comprise a cholesterol esterase, a cholesterol oxidase, a peroxidase (such as horseradish peroxidase), 4-aminoantipyrene, ALPS, α-cyclodextrin sulfate, dextran sulfate, magnesium chloride, a surfactant (e.g., Triton X-100 and/or pluronic L64), and a buffer. A suitable buffer may be, for example, a phosphate buffer, and a suitable pH may be in the range of between about pH 5 to about pH 9, or between about pH 6 and about 8, optionally between about pH 6.8 and about pH 7.8, e.g. about pH 7.4. A suitable cholesterol esterase for use in such a composition may comprise a bacterial cholesterol esterase, such as, for example, a cholesterol esterase from a *Pseudomonas* bacterium, and a suitable cholesterol oxidase may comprise a bacterial cholesterol oxidase, such as a cholesterol oxidase from a *Pseudomonas* bacterium.

Applicants disclose herein a kit comprising reagents for use in an assay for the simultaneous, rapid measurement of at least two of TC, LDL-C and HDL-C in a sample of blood from a subject without substantial precipitation of said lipoproteins. Embodiments of the kits disclosed herein may comprise a first container containing a first reagent comprising a lipoprotein solubilization agent, a lipoprotein interactant, and a buffer; and a second container containing a second reagent comprising a buffer, an amphiphilic agent, a lipase, an oxidase, and a colorant. Embodiments of the kits disclosed herein may comprise a first container containing a first reagent comprising a lipoprotein solubilization agent, a lipoprotein interactant, and a buffer; and a second container containing a second reagent comprising a buffer, an amphiphilic agent, a cholesterol esterase, a cholesterol oxidase, and a colorant. In embodiments, a colorant may comprise a peroxidase, a substrate for a peroxidase, or both.

Embodiments of the kits disclosed herein may comprise a first container containing a first reagent comprising a lipoprotein solubilization agent, a lipoprotein interactant, and a buffer; a second container containing a second reagent comprising a buffer, an amphiphilic agent, a lipase, an oxidase, and a colorant; and instructions for their use. In embodiments, such kits comprise a first container containing a first reagent comprising a lipoprotein solubilization agent, a lipoprotein interactant, and a buffer; a second container containing a second reagent comprising a buffer, an amphiphilic agent, a cholesterol esterase, a cholesterol oxidase, and a colorant; and instructions for their use. In embodiments, a colorant may comprise a peroxidase and a substrate for a peroxidase.

Also disclosed herein are methods for the simultaneous, rapid measurement of at least two of TC, LDL-C and HDL-C in a sample of blood from a subject without substantial precipitation of said lipoproteins. Embodiments of methods for the simultaneous, rapid measurement of TC, LDL-C and HDL-C in a sample of blood from a subject without substantial precipitation of said lipoproteins comprise steps of: combining at an initial time at least a portion of said sample of blood with a first reagent comprising a lipoprotein solubilization agent, a lipoprotein interactant, and a buffer to provide a combined solution; adding to said combined solution a second reagent comprising a buffer, an amphiphilic agent, a lipase, an oxidase, and a colorant to provide a colored solution; and measuring absorbance of light by said colored solution within a first time period, within a second time period, and within a third time period after addition of said second reagent.

In embodiments of such methods, said first time period comprises a time period of less than about 3 minutes after said initial time, and said third time period comprises a time period of greater than about 5 minutes after said initial time, where said initial time comprises the time at which said second reagent is added to said combined solution.

In embodiments, said methods for the simultaneous, rapid measurement of TC, LDL-C and HDL-C in a sample of blood from a subject without substantial precipitation of said lipoproteins comprise steps of: combining at an initial time at least a portion of said sample of blood with a first reagent comprising a lipoprotein solubilization agent, a lipoprotein interactant, and a buffer to provide a combined solution; adding to said combined solution a second reagent comprising a buffer, an amphiphilic agent, a cholesterol esterase, a cholesterol oxidase, and a colorant to provide a colored solution; and measuring absorbance of light by said colored solution within a first time period, within a second time period, and within a third time period.

In embodiments of such methods, said first time period comprises a time period of less than about 3 minutes after said initial time, and said third time period comprises a time period of greater than about 5 minutes after said initial time, where said initial time comprises the time at which said second reagent is added to said combined solution.

In embodiments of the methods disclosed herein, the first time period may comprise a time period of between about 0 minutes to about 2 minutes after said initial time, the second time period may comprise a time period of between about 2 minutes to about 6 minutes after said initial time, and the third time period may comprise a time period of between about 6 minutes to about 10 minutes, or longer. In embodiments, said third time period comprises an open-ended time period including any time after about 5 minutes or about 6 minutes after said initial time. In embodiments, the initial time is the time at which the second reagent is added to the solution.

It will be understood that other times and time periods may also be used, e.g., longer times and time periods may be used where the amounts of lipase, or oxidase, or both, are decreased. It will also be understood that, e.g., shorter times and time periods may be used where the amounts of lipase, or oxidase, or both, are increased. Similarly, other times and time periods may also be used where the amounts of lipoprotein solubilization agents and/or lipoprotein interactants are altered. Accordingly, in further embodiments of the methods disclosed herein, the time periods may be longer than the time periods discussed above; for example, reagents and methods may be configured where the first time period may comprise a time period of between about 0 minutes to about 10 minutes after said initial time, the second time period may comprise a time period of between about 10 minutes to about 20 minutes or about 30 minutes after said initial time, and the third time period may comprise a time period of between about 20 minutes to about 40 minutes, or between about 30 minutes to about 60 minutes, or longer. In yet further embodiments of the methods disclosed herein, the time periods may be shorter than the time periods discussed above; for example, reagents and methods may be configured where the first time period may comprise a time period of between about 0 minutes to about 1 minute after said initial time, the second time period may comprise a time period of between about 1 minutes to about 4 minutes or to about 5 minutes after said initial time, and the third time period may comprise a time period of between about 4 minutes to about 8 minutes, or between about 5 minutes to about 9 minutes.

In embodiments, a step of measuring absorbance may comprise measuring absorbance using a spectrophotometer. A step of measuring absorbance will typically comprise measuring absorbance at or near a particular frequency using a spectrophotometer. In embodiments, a step of measuring absorbance may comprise measuring absorbance at or near a wavelength of about 560 nm. In embodiments, a step of measuring absorbance may further comprise using a spectrophotometer to measure the difference in absorbance at or near to a first wavelength and the absorbance at or near to a second wavelength; such a difference in absorbance measured at two wavelengths may be termed "$\Delta A$." For example, such two wavelengths may be about 560 nm and about 700 nm. In embodiments, a step of measuring absorbance may further comprise using a spectrophotometer to measure absorbance at a wavelength of about 560 nm and at a wavelength of about 700 nm effective to obtain the difference in absorbance between about 560 nm and about 700 nm. It will be understood that for some colorants, other wavelengths, and other wavelength intervals, may be used; for example, there are chromogenic peroxidase substrates that may be detected at wavelengths between about 400 nm and about 700 nm.

Such absorbance measurements may be made at a particular time, or at two particular times, or at three, or more, particular times, where a particular time is defined with respect to an initial time. Measurements at a particular time may include measurements made during a range of times, such as between 0 to about 2 minutes after an initial time, or between about 2 minutes and about 6 minutes after an initial time, or between about 6 minutes and about 10 minutes after an initial time, or at other times and/or other time periods.

In embodiments, a step of measuring absorbance may comprise measuring absorbance using a spectrophotometer at two times, and recording or calculating the difference between the measurements made at said two times. In embodiments, absorbance may be $\Delta A$ measured as the difference in absorbance measured at two wavelengths, and the difference of the $\Delta A$ measured at a first time and the $\Delta A$ measured at a second time may be recorded or calculated; such a difference between ΔA measured at two times may be termed "ΔA$_t$." For example, ΔA$_t$ may be measured by measuring ΔA as the difference between absorbance measured at 560 nm and at 700 nm, where the ΔA measurement is made at about 2 minutes after an initial time and at about 6 minutes after an initial time, where ΔA$_t$ is the difference between the two ΔA measurements. In further embodiments, ΔA$_t$ may be measured by measuring ΔA as the difference between absorbance measured at 560 nm and at 700 nm, where the ΔA measurement is made at an initial time and at about 2 minutes after an initial time, where ΔA$_t$ is the difference between the two ΔA measurements. In further embodiments, ΔA$_t$ may be measured by measuring ΔA as the difference between absorbance measured at 560 nm and at 700 nm, where the ΔA measurement is made at about 6 minutes after an initial time and at about 10 minutes after an initial time, where ΔA$_t$ is the difference between the two ΔA measurements. In further embodiments, where the ΔA measurement is to be made after a particular time, it will be understood that phrases such as, e.g., "after about 5 minutes", "after about 10 minutes", "at a time period greater than about 5 minutes", "at a time period greater than about 10 minutes", and the like, may be measured between any time after the stated time and a reasonable time thereafter. In embodiments, such a time period for measurement may not extend in time beyond about 30 minutes, or beyond about 20 minutes, after the initial time.

In embodiments, a first reagent may comprise a lipoprotein solubilization agent, a lipoprotein interactant, and a buffer. In embodiments, a lipoprotein solubilization agent may comprise a surfactant. In embodiments, a lipoprotein interactant may comprise a dextran (such as a dextran derivative such as a sulfonated or phosphorylated dextran), a cyclodextrin (such as a cyclodextrin derivative such as a sulfonated or methylated cyclodextrin), a negatively charged natural product such as heparin, or combinations thereof. In embodiments, a lipoprotein interactant may comprise a low molecular weight negatively charged dextran ester, e.g., a low molecular weight dextran sulfate. In embodiments, a lipoprotein interactant may comprise an α-cyclodextrin derivative such as an α-cyclodextrin sulfate ester. In embodiments, a first reagent may comprise a peroxidase substrate. In embodiments, a peroxidase substrate may comprise an aminoantipyrene compound, such as 4-aminoantipyrene and an aniline-containing compound, such as ALPS. In further embodiments, the first reagent may comprise α-cyclodextrin sulfate, dextran sulfate, magnesium chloride, 4-aminoantipyrene, ALPS, and a buffer, such as, for example, a phosphate buffer (e.g., Na$_x$PO$_4$ (where Na$_x$PO$_4$ is a sodium phosphate salt; e.g., may be NaH$_2$PO$_4$, Na$_2$HPO$_4$, or Na$_3$PO$_4$) for buffering the pH to between about pH 6 to about pH 8. For example, in embodiments, the first reagent may comprise α-cyclodextrin sulfate (1 mM), dextran sulfate (20 μM), magnesium chloride (4 mM), 4-aminoantipyrene (2.25 mM), 3 mM ALPS, and Na$_x$PO$_4$ (100 mM), pH about 7.

In embodiments, components of a peroxidase substrate may be separated into different reagents. Separation of peroxidase substrate components into different reagents may be desired for stability of one or both of the reagents, or may be useful to reduce or prevent degradation of one or both of the reagents. Thus, in embodiments, a first reagent may include an antipyrene compound, and a second reagent may include an aniline-containing compound. In further embodiments, a first reagent may comprise 4-aminoantipyrene and a second reagent may comprise N-Ethyl-N-(2-hydroxy-3-sulfopropyl)-3,5-dimethoxyaniline (ALPS). In further embodiments, a first reagent may comprise between about 1 mM and about 5 mM 4-aminoantipyrene and a second reagent may comprise between about 0.5 mM and about 20 mM ALPS. For example, a first reagent may comprise 2.25 mM 4-aminoantipyrene and a second reagent may comprise 3 mM ALPS.

In embodiments, components of a peroxidase substrate may be contained in a single reagent. Including multiple components in a single reagent may be desired for simplicity of manufacture, or ease of use, or for other reasons. For example, a reagent containing all components of a peroxidase substrate may comprise an aminoantipyrene compound and an aniline-containing compound. In further embodiments, a reagent containing all components of a peroxidase substrate may comprise 4-aminoantipyrene and N-Ethyl-N-(2-hydroxy-3-sulfopropyl)-3,5-dimethoxyaniline (ALPS). In further embodiments, a reagent containing all components of a peroxidase substrate may comprise between about 1 mM and about 5 mM 4-aminoantipyrene and between about 0.5 mM and about 20 mM ALPS. For example, a reagent containing all components of a peroxidase substrate may comprise 2.25 mM 4-aminoantipyrene and 3 mM ALPS. In other embodiments, reagents may be dried so as to increase stability. Reagents may be lyophilized or provided as glassy films, e.g., films which may adhere to a container wall. When such reagents are dried, they may be formulated so as to dissolve rapidly (e.g., within seconds to minutes) upon addition of water or of another aqueous solvent such as a buffer solution.

In embodiments of the methods disclosed herein, a second reagent may comprise a lipase, an oxidase, and a colorant. In embodiments of said second reagent, a lipase may comprise a cholesterol esterase, an oxidase may comprise a cholesterol oxidase, and a colorant may comprise a peroxidase. In embodiments of the methods disclosed herein, a second reagent may comprise a buffer, an amphiphilic agent, a cholesterol esterase, a cholesterol oxidase, and a colorant. In embodiments of the methods disclosed herein, an amphiphilic agent may comprise a surfactant. In embodiments, a colorant may comprise a peroxidase, a peroxidase substrate, and may comprise both a peroxidase and a peroxidase substrate. A peroxidase may comprise, for example, a peroxidase from horseradish (*Armoracia rusticana*) (HRP). A peroxidase substrate may comprise an aniline-containing compound, an aminoantipyrene compound or both. In embodiments, a colorant may comprise an aminoantipyrene compound, such as 4-aminoantipyrene. In embodiments, a colorant may comprise N-Ethyl-N-(2-hydroxy-3-sulfopropyl)-3,5-dimethoxyaniline (ALPS). In embodiments of the methods disclosed herein, a second reagent may comprise a bacterial cholesterol esterase, such as a cholesterol esterase from a *Pseudomonas* bacterium, and in embodiments may comprise a bacterial cholesterol oxidase, such as a bacterial cholesterol oxidase from a *Pseudomonas* bacterium. In embodiments of the methods disclosed herein, a second reagent may comprise a buffer, such as a phosphate buffer (e.g., Na$_x$PO$_4$ (50 mM)), Triton X-100 (0.06%), pluronic L64 (3 g/L), N-Ethyl-N-(2-hydroxy-3-sulfopropyl)-3,5-dimethoxyaniline (ALPS) (3 mM), cholesterol esterase from *Pseudomonas* sp. (750 U/L), and cholesterol oxidase from *Pseudomonas* sp. (1.5 kU/L).

In embodiments, a composition as disclosed herein may comprise α-cyclodextrin sulfate, dextran sulfate, magnesium chloride, a peroxidase substrate (e.g., diaminobenzidine, or 4-aminoantipyrene and ALPS), cholesterol esterase (e.g., cholesterol esterase from *Pseudomonas* sp.), cholesterol oxidase (e.g., cholesterol oxidase from *Pseudomonas* sp.), a surfactant, and a buffer. In embodiments, a composition as disclosed herein may comprise a first reagent and a second reagent. In embodiments, a composition as disclosed herein may comprise a first reagent, a second reagent, and at least a portion of a sample of blood from a subject.

A buffer, for example, may be a phosphate buffer (e.g., $Na_xPO_4$ (where $Na_xPO_4$ is a sodium phosphate salt; e.g., may be $NaH_2PO_4$, $Na_2HPO_4$, or $Na_3PO_4$) for buffering the pH to between about pH 5 to about pH 9, or between about pH 6 to about pH 8, optionally between about pH 6.8 to about pH 7.8, e.g., pH 7.4. In embodiments, a composition as disclosed herein may comprise between about 100 U/L to about 2000 U/L of cholesterol esterase from *Pseudomonas* sp. (e.g., about 750 U/L), and may comprise between about 100 U/L to about 3000 U/L cholesterol oxidase from *Pseudomonas* sp. (e.g., about 1.5 kU/L).

In embodiments, for example, a peroxidase substrate may comprise between about 1 mM and about 5 mM 4-aminoantipyrene and between about 0.5 mM and about 20 mM ALPS, e.g., about 2.25 mM 4-aminoantipyrene and about 3 mM ALPS. In embodiments, a surfactant may be, for example, Triton X-100 and/or pluronic L64, e.g., the composition may comprise about 0.01 to about 1% Triton X-100 and may comprise about 1 to about 10 g/L/or pluronic L64; in particular embodiments, the composition may comprise about 0.06% Triton X-100 and about 3 g/L pluronic L64.

In embodiments of the methods disclosed herein, a measurement within a first time period may be used to determine HDL-cholesterol in said sample. In embodiments of the methods disclosed herein, a measurement within a second time period may be used to determine LDL-cholesterol in said sample. In embodiments of the methods disclosed herein, a measurement within a third time period may be used to determine total cholesterol in said sample. In embodiments of the methods disclosed herein, a measurement may comprise measuring absorbance using a spectrophotometer. In embodiments of the methods disclosed herein, a measurement may comprise measuring $\Delta A$ (where $\Delta A$ is the difference between absorbance measured at the first wavelength and at the second wavelength) using a spectrophotometer. In embodiments of the methods disclosed herein, a measurement may comprise measuring $\Delta A_t$ (where $\Delta A_t$ is the difference between absorbance measured at a first time and the absorbance measured at a second time) using a spectrophotometer. Absorbance measurements for measuring $\Delta A_t$ may be $\Delta A$ measurements.

In embodiments of the methods disclosed herein, a method of analyzing cholesterol measurement data obtained from a blood sample of a subject may comprise steps of: measuring product formation from a reaction between cholesterol sub-fractions and a reagent mixture comprising a lipase and an oxidase within a first time period, within a second time period, and within a third time period to provide cholesterol measurement data; wherein a low density lipoprotein-cholesterol (LDL-C) measurement is obtained from said cholesterol measurement data obtained within said second time period; wherein a total cholesterol (TC) measurement is obtained from said cholesterol measurement data obtained within said third time period; and wherein a high density lipoprotein-cholesterol (HDL-C) measurement is obtained from said cholesterol measurement data obtained within said second time period plus the rate of product formation measured in said first time period; whereby said cholesterol measurement data obtained from a blood sample of a subject is analyzed.

In particular embodiments of the methods of analyzing cholesterol measurement data obtained from a blood sample of a subject disclosed herein, said lipase may comprise a cholesterol esterase, and said oxidase may comprise a cholesterol oxidase. For example, in embodiments of the methods disclosed herein, a method of analyzing cholesterol measurement data obtained from a blood sample of a subject may comprise steps of: measuring product formation from a reaction between cholesterol sub-fractions and a reagent mixture comprising a cholesterol esterase and a cholesterol oxidase within a first time period, within a second time period, and within a third time period to provide cholesterol measurement data; wherein a LDL-C measurement is obtained from said cholesterol measurement data obtained within said second time period; wherein a TC measurement is obtained from said cholesterol measurement data obtained within said third time period; and wherein a HDL-C measurement is obtained from said cholesterol measurement data obtained within said second time period plus the rate of product formation measured in said first time period; whereby said cholesterol measurement data obtained from a blood sample of a subject is analyzed.

Embodiments of a method of analyzing cholesterol measurement data obtained from a blood sample of a subject may comprise steps wherein said first time period may comprise less than about 3 minutes after an initial time, wherein said initial time comprises the time at which a second reagent is added to a combined solution, and wherein a combined solution may comprise a first reagent and at least a portion of a blood sample. In embodiments, a method of analyzing cholesterol measurement data obtained from a blood sample of a subject may comprise a step wherein a third time period comprises a time period of greater than about 5 minutes after said initial time, wherein said initial time comprises the time at which a second reagent is added to a combined solution. In embodiments, said first time period comprises a time period of between about 0 minutes to about 2 minutes after said initial time, said second time period comprises a time period of between about 2 minutes to about 6 minutes after said initial time, and said third time period comprises a time period of between about 6 minutes to about 10 minutes, or longer. In embodiments, said third time period may comprise an open-ended time period, effective to include any time greater than about 5 minutes after said initial time, or greater than about 6 minutes after said initial time.

In embodiments, a step of measuring product formation comprises measuring absorbance. In embodiments, a step of measuring absorbance comprises measuring $\Delta A$ using a spectrophotometer. In further embodiments, a step of measuring absorbance using a spectrophotometer comprises measuring absorbance at a first wavelength and measuring absorbance at a second wavelength to obtain a $\Delta A$ measurement, where $\Delta A$ is the difference between absorbance measured at the first wavelength and at the second wavelength. In embodiments, a step of measuring $\Delta A$ using a spectrophotometer comprises measuring $\Delta A$ at a wavelength of between about 300 nm to about 700 nm, and at a wavelength of between about 600 nm to about 900 nm. In more particular embodiments, a step of measuring $\Delta A$ using a spectrophotometer comprises measuring $\Delta A$ at a wavelength of about 560 nm and at a wavelength of about 700 nm.

In at least some embodiments, methods disclosed herein include further methods of analyzing cholesterol measurement data obtained from a blood sample of a subject, wherein an HDL-C measurement is obtained from said cholesterol measurement data obtained within a second time period plus the rate of product formation measured in a first time period according to the following formula:

$$K_1 - K_2 \times (\text{LDL-C}) + K_3 \times R_1$$

where $K_1$ is a constant whose value may be between about 0 to about 250;

where $K_2$ is a constant whose value may be between about 0 to about 100;

where the amount of LDL-C may be determined by the difference in absorbance measured between the beginning of said second time period and the end of said second time period;

where $K_3$ is a constant whose value may be between about 1 to about 20,000; and where $R_1$ may be determined by the difference in absorbance measured between the beginning of said first time period and the end of said first time period, and wherein said time periods may be determined with respect to an initial time, wherein the initial time period comprises the time at which a second reagent is added to a combined solution comprising a first reagent and at least a portion of said blood sample.

In embodiments, the value of $K_1$ may be between about 0 to about 100, or between about 0 to about 50. In embodiments, the value of $K_2$ may be between about 0 to about 50, or between about 0 to about 25. In embodiments, the value of $K_3$ may be between about 0 to about 10,000, or between about 0 to about 5,000. In further embodiments, the value of $K_1$ may be between about 0 to about 25, or between about 0 to about 10. In further embodiments, the value of $K_2$ may be between about 0 to about 5, or between about 0 to about 2.

In embodiments of further methods of analyzing cholesterol measurement data obtained from a blood sample of a subject, a first time period may comprise a time period of between about 0 minutes to about 2 minutes after an initial time. In embodiments, a second time period may comprise a time period of between about 2 minutes to about 6 minutes after an initial time. In embodiments, a third time period may comprise a time period of between about 6 minutes to about 10 minutes after an initial time, or longer. In embodiments, said third time period may comprise an open-ended time period, effective to include any time greater than about 5 minutes after said initial time, or greater than about 6 minutes after said initial time.

In embodiments of further methods of analyzing cholesterol measurement data obtained from a blood sample of a subject, $K_1$ may have a value between about 0 to about 3. In embodiments of further methods of analyzing cholesterol measurement data obtained from a blood sample of a subject, $K_2$ may have a value between about 0 to about 1. In embodiments of further methods of analyzing cholesterol measurement data obtained from a blood sample of a subject, $K_3$ may have a value between about 800 to about 1,800. In embodiments of further methods of analyzing cholesterol measurement data obtained from a blood sample of a subject, $K_1$ may have a value of about 1.30. In embodiments of further methods of analyzing cholesterol measurement data obtained from a blood sample of a subject, $K_2$ may have a value of about 0.446. In embodiments of further methods of analyzing cholesterol measurement data obtained from a blood sample of a subject, $K_3$ may have a value of about 1255.

In embodiments of further methods of analyzing cholesterol measurement data obtained from a blood sample of a subject, cholesterol measurement data may comprise data from an absorbance measurement. In embodiments of further methods of analyzing cholesterol measurement data obtained from a blood sample of a subject, absorbance measurements may comprise absorbance measurements made using a spectrophotometer. In embodiments of further methods of analyzing cholesterol measurement data obtained from a blood sample of a subject, an absorbance measurement using a spectrophotometer may comprise a $\Delta A$ measurement, where a $\Delta A$ measurement comprises an absorbance measurement made at a first wavelength and an absorbance measurement made at a second wavelength, effective to obtain the difference in absorbance at said first wavelength and at said second wavelength. In embodiments of further methods of analyzing cholesterol measurement data obtained from a blood sample of a subject, a measurement of $\Delta A$ using a spectrophotometer may comprise absorbance measurements at a wavelength of about 560 nm and at a wavelength of about 700 nm.

Applicants further disclose herein devices for measuring total cholesterol or a cholesterol sub-fraction in at least a portion of a sample of blood from a subject. In embodiments, a device for measuring total cholesterol or a cholesterol sub-fraction in at least a portion of a sample of blood from a subject may comprise: means for combining a first reagent with at least a portion of a sample of blood from a subject, effective to provide a combined solution; means for combining a second reagent with said combined solution to provide a colored solution; means for measuring an optical property of said colored solution; and means for displaying or reporting the results of said measurement of said optical property of said colored solution. In further embodiments, a device for measuring total cholesterol or a cholesterol sub-fraction in at least a portion of a sample of blood from a subject may comprise: a chamber for combining a first reagent with at least a portion of a sample of blood from a subject, effective to provide a combined solution; a conduit for combining a second reagent with said combined solution to provide a colored solution; an optical detector for measuring an optical property of said colored solution; and a display element or a communication link for reporting the results of said measurement of said optical property of said colored solution. In embodiments, a display element and/or communication link may be suitable for two-way communication.

Applicants disclose herein systems for measuring total cholesterol or a cholesterol sub-fraction in at least a portion of a sample of blood from a subject. In embodiments, a system for measuring total cholesterol or a cholesterol sub-fraction in at least a portion of a sample of blood from a subject comprises a device as disclosed herein, and a means for communicating information from said device to a computer, a computer network, a telephone, a telephone network, or a device configured to display information communicated from said device. It will be understood that a means for communicating information may include means for one-way communication and may include means for two-way communication, and may include means for communication with multiple locations or entities. In embodiments, a system for measuring total cholesterol or a cholesterol sub-fraction in at least a portion of a sample of blood from a subject comprises a device as disclosed herein, and a channel for communicating information from said device to a computer, said wherein said channel is selected from a computer network, a telephone network, a metal communication link, an optical communication link, and a wireless communication link. It will be understood that a channel for communicating information may be a one-way communication channel and may be a two-way communication channel, and may include channels for communication with multiple locations or entities.

In embodiments, triglyceride levels may be determined by methods in which a sample of blood is contacted with a lipase to provide fatty acids and glycerol from TG in the blood sample. This glycerol may be contacted with a kinase, such as glycerol kinase, to provide glycerol phosphate, which may be contacted with an oxidase, such as glycerol 3-phosphate oxidase, to provide dihydroxyacetone phosphate and hydrogen peroxide. Colorants, such as 4-amino-antipyrene and N-Ethyl-N-(sulfopropyl aniline) may be contacted with horseradish peroxidase in the presence of the hydrogen peroxide effective to form a dye, such as a quinoneimine dye, the measurement of which dye provides a measure of the TG level in the blood sample. Such a dye may be measured by spectrophotometric means; for example, such a dye may be measured, and TG levels determined, by measuring absorbance at a frequency (e.g., 560 nm), or within a frequency range (e.g., 555 nm to 565 nm).

VLDL-C may be estimated from TG measurements by dividing the concentration of TG in a sample by 5:

$$\text{VLDL-C} = \text{TG}/5$$

in order to provide a value for the level of VLDL-C in blood sample in which TG has been measured. The level of VLDL-C estimated in this way may further be used to calculate the TC in a blood sample by adding the levels of HDL-C, LDL-C, and VLDL-C (as estimated according to the formula VLDL-C=TG/5).

However, in place of such an estimate, Applicants disclose herein further methods to calculate VLDL-C based on the novel and useful measurements of HDL-C, LDL-C, TC, and TG disclosed herein. These further methods are believed to provide greater accuracy than prior methods. In embodiments, VLDL-C may be calculated from HDL-C, TC, and TG measurements, where these measurements are made according to the methods disclosed herein. In embodiments, VLDL-C may be calculated from HDL-C, LDL-C, TC, and TG measurements, where these measurements are made according to the methods disclosed herein.

In embodiments, the level of VLDL-C in a single sample, or a single portion of a sample, of blood of a subject may be calculated from HDL-C, TC, and TG measurements, for example, by the relation:

$$\text{VLDL-C} = \alpha\text{TC} + \beta\text{HDL-C} + \delta\text{TG} + a_1(\text{TG}+\varepsilon)(\text{TC}+\kappa) + \lambda$$

where $\alpha$, $\beta$, $\delta$, and $a_1$ are constants which multiply TC, HDL-C, TG, and (TG+$\varepsilon$)(TC-$\kappa$), respectively; and where $\varepsilon$, $\kappa$, and $\lambda$ are additive constants to be added to TG, TC, and the sum of all other factors, respectively. The term "(TG+$\varepsilon$)(TC+$\kappa$)" may be called a "cross-term" in which the terms in one parenthesis multiply the terms in the other parenthesis. The multiplicative constants $\alpha$, $\beta$, $\delta$, and $a_1$ and the additive constants $\varepsilon$, $\kappa$, and $\lambda$ may take any value, whether positive, negative, or zero.

In embodiments, the level of VLDL-C in a single sample, or a single portion of a sample, of blood of a subject may be calculated from HDL-C, LDL-C, TC, and TG measurements, for example, by the relation:

$$\text{VLDL-C} = \alpha\text{TC} + \beta\text{HDL-C} + \gamma\text{LDL-C} + \delta\text{TG} + a_1(\text{TG}+\varepsilon)(\text{TC}+\kappa) + \lambda$$

where $\alpha$, $\beta$, $\gamma$, $\delta$, and $a_1$ are constants which multiply TC, HDL-C, LDL-C, TG, and (TG+$\varepsilon$)(TC+$\kappa$), respectively; and where $\varepsilon$, $\kappa$, and $\lambda$ are additive constants to be added to TG, TC, and the sum of all other factors, respectively. The multiplicative constants $\alpha$, $\beta$, $\gamma$, $\delta$, and $a_1$ and the additive constants $\varepsilon$, $\kappa$, and $\lambda$ may take any value, whether positive, negative, or zero. As indicated above, and as used elsewhere herein, the term "(TG+$\varepsilon$)(TC+$\kappa$)" and similar terms may be called a "cross-term" in which the terms in one parenthesis multiply the terms in the other parenthesis.

It will be understood that, in embodiments, all possible cross-terms, and all possible combinations of cross-terms may be included in relationships used to calculate VLDL-C. Thus, for example, in addition to, and/or in place of, the cross-term (TG+$\varepsilon$)(TC+$\kappa$), any or all of the following cross-terms may be included in relationships used to calculate VLDL-C: (TG+$\varepsilon$)(HDL-C+$\mu$); (TG+$\varepsilon$)(LDL-C+$\nu$); (TC+$\kappa$)(HDL-C+$\mu$); (TC+$\kappa$)(LDL-C+$\nu$); and (LDL-C+$\nu$)(HDL-C+$\mu$), where the additive constants $\lambda$, $\varepsilon$, $\kappa$, $\mu$, and $\nu$ may take any value, whether positive, negative, or zero.

Accordingly, in embodiments, VLDL-C may be calculated from the measured quantities as follows:

$$\text{VLDL-C} = \alpha\text{TC} + \beta\text{HDL-C} + \gamma\text{LDL-C} + \delta\text{TG} + + a_1(\text{TG}+\varepsilon)(\text{TC}+\kappa) + a_2(\text{TG}+\varepsilon)(\text{HDL-C}+\mu) + a_3(\text{TG}+\varepsilon)(\text{LDL-C}+\nu) + a_4(\text{TC}+\kappa)(\text{HDL-C}+\mu) + a_5(\text{TC}+\kappa)(\text{LDL-C}+\nu) + a_6(\text{LDL-C}+\nu)(\text{HDL-C}+\mu)$$

where the multiplicative coefficients $\alpha$, $\beta$, $\gamma$, $\delta$, $a_1$, $a_2$, $a_3$, $a_4$, $a_5$, and $a_6$, may take any value, whether positive, negative, or zero; and where the additive constants $\lambda$, $\varepsilon$, $\kappa$, $\mu$, and $\nu$ may take any value, whether positive, negative, or zero.

In yet further embodiments, the level of VLDL-C in a single sample, or a single portion of a sample, of blood of a subject may be calculated from other relationships using some or all of the measured values of TC, TG, HDL-C, and LDL-C and multiplicative and additive constants similar in form to the relationships provided above.

Applicants further disclose herein methods, devices and systems for measuring, in one device, at least two biologically relevant attributes of a sample. In embodiments, a biologically relevant attribute of a sample includes, without limitation, a lipoprotein level including TC, HDL-C, LDL-C, and VLDL-C; blood triglyceride (TG) level; blood hematocrit; blood iron content; erythrocyte sedimentation rate (ESR); a cytometric measurement (e.g., determination of the presence and/or amounts, including fractional amounts and/or absolute amounts of a cell type or cell types) including antibody based, dye-based, flow-cytometric, imaging, and other measurements of cells, cell number, cell type, and cellular properties in a sample; a chemical measurement including a measurement of pH, of a salt concentration (e.g., of a cation and/or anion which makes up a salt), presence of and/or concentration of a vitamin, a protein, a metabolite of a protein or small molecule, a marker indicative of a medical condition, and other measurements of blood, urine, tissue, or other biological sample. The measurements of at least two biologically relevant attributes of a sample may be made simultaneously, or may be made in succession, or, where at least three measurements of biologically relevant attributes of a sample are made, some measurements may be made simultaneously while other measurements of biologically relevant attributes of a sample may be made before or after the measurements that are made simultaneously.

In embodiments, one or more of such measurements may be rapid measurements, where a rapid measurement is one that may be made within a time period of about one hour; or may be made within a time period of about one half an hour; or may be made within a time period of about one quarter of an hour; or may be made within a time period of about ten minutes; or may be made within a time period of about 5 minutes; or may be made within a time period of about 4 minutes; or may be made within a time period of about 3 minutes; or may be made within a time period of about 2 minutes; or may be made within a time period of about 1 minute; or may be made within a time period of about 30 seconds; or may be made within a time period of about 15 seconds; or may be made within a time period of about 10 seconds; or may be made within a time period of about 5 seconds; or may be made within a time period of about 1 second.

In embodiments, one or more of such measurements may be made using a small volume blood sample, or no more than a small volume portion of a blood sample, where, a small volume blood sample, and a small volume portion of a blood sample, comprises no more than about 5 mL; or comprises no more than about 3 mL; or comprises no more than about 1 mL; or comprises no more than about 250 µL; or comprises no more than about 100 µL; or comprises no more than about 50 µL; or comprises no more than about 25 µL; or comprises no more than about 20 µL; or comprises no more than about 15 µL; or comprises no more than about 10 µL; or comprises no more than about 5 µL; or comprises no more than about 1 µL; or comprises other small volume, e.g., as described herein.

In embodiments of devices and systems disclosed herein, a device may comprise a device for measuring both a) TC or a cholesterol sub-fraction in at least a portion of a sample of blood from a subject, and b) another attribute of said sample of blood from the subject. In embodiments, said other attribute may be measured on a different portion of the sample of blood from the subject than the portion used to measure TC or a cholesterol sub-fraction. In embodiments, said other attribute may be measured on the same portion of the sample of blood from the subject as is used to measure TC or a cholesterol sub-fraction. In embodiments, a device for measuring both a) TC or a cholesterol sub-fraction in at least a portion of a sample of blood from a subject, and b) another attribute of said sample of blood from the subject may comprise: means for combining a first reagent with at least a portion of a sample of blood from a subject, effective to provide a combined solution; means for combining a second reagent with said combined solution to provide a colored solution; means for measuring an optical property of said colored solution; means for displaying or reporting the results of said measurement of said optical property of said colored solution; and means for measuring another attribute of said sample of blood from the subject. In embodiments, a device for measuring both a) TC or a cholesterol sub-fraction in at least a portion of a sample of blood from a subject, and b) another attribute of said sample of blood from the subject may be configured for, and able to, make any two or more of a plurality of measurements on a sample, such as a blood sample. In embodiments of a device for measuring both a) TC or a cholesterol sub-fraction in at least a portion of a sample of blood from a subject, and b) another attribute of said sample of blood from the subject, said measurements may be selectable effective that some or all of a plurality of measurements are selected for measurement of a first sample, and a different selection of some or all of said plurality of measurements may be selected for measurements to be performed on a second sample.

In further embodiments, a device for measuring both a) TC or a cholesterol sub-fraction in at least a portion of a sample of blood from a subject, and b) another attribute of said sample of blood from the subject may comprise: a chamber for combining a first reagent with at least a portion of a sample of blood from a subject, effective to provide a combined solution; a conduit for combining a second reagent with said combined solution to provide a colored solution; an optical detector for measuring an optical property of said colored solution; a centrifuge; and a display element or a communication link for reporting the results of said measurement of said optical property of said colored solution. In embodiments of such a device, the device may be configured for, and able to, make any two or more of a plurality of measurements on the sample. In embodiments of such a device, said measurements may be selectable effective that some or all of a plurality of measurements are selected for measurement of a first sample, and a different selection of some or all of said plurality of measurements may be selected for measurements to be performed on a second sample.

Systems for measuring total cholesterol or a cholesterol sub-fraction in at least a portion of a blood sample, and another biologically relevant attribute from said blood sample from a subject may include a device for measuring both a) TC or a cholesterol sub-fraction in at least a portion of a sample of blood from a subject, and b) another attribute of said sample of blood from the subject. In embodiments, such a system comprises a device for measuring both a) and b) as disclosed herein, and a means for communicating information from said device to a computer, a computer network, a telephone, a telephone network, or a device configured to display information communicated from said device. In embodiments, a system for measuring both a) TC or a cholesterol sub-fraction in at least a portion of a sample of blood from a subject, and b) another attribute of said sample of blood from the subject comprises a device as disclosed herein, and a channel for communicating information from said device to a computer, said wherein said channel is selected from a computer network, a telephone network, a metal communication link, an optical communication link, and a wireless communication link. Systems as disclosed herein may comprise a device configured for, and able to, make any two or more of a plurality of measurements on the sample. In embodiments of systems comprising such a device, said measurements may be selectable effective that some or all of a plurality of measurements are selected for measurement of a first sample, and a different selection of some or all of said plurality of measurements may be selected for measurements to be performed on a second sample.

Embodiments of systems for measuring total cholesterol or a cholesterol sub-fraction in at least a portion of a blood sample, and another biologically relevant attribute from said blood sample from a subject may include a device as disclosed in U.S. Pat. No. 8,088,593 or U.S. application Ser. No. 13/244,947 filed Sep. 26, 2011, both fully incorporated herein by reference for all purposes, and may include systems as disclosed therein. For example, systems as disclosed herein may include a communication assembly for transmitting or receiving a protocol based on the analyte to be detected or based on other analytes to be detected by the device or system. For example, in embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Assays, methods, reagents, kits, devices, and systems as disclosed herein provide advantages over prior assays, methods, reagents, kits, and systems by allowing the rapid and inexpensive measurement of cholesterol and cholesterol sub-fractions in a single assay. The methods and assays disclosed herein allow for measurement of multiple lipoprotein fractions on the same sample of blood, or on the same portion of a sample of blood; for example, HDL-C, LDL-C, and TC may be measured on the same sample of blood, or on the same portion of a sample of blood. These measurements are made without substantial precipitation of lipoproteins in the sample, or sample portion. Providing desired measurements in a single assay simplifies procedures, reduces likelihood of error, reduces variability of results, and allows for more rapid and more inexpensive procedures. The disclosed assays, methods, reagents, kits, and systems are effective to reduce the number of assays required to determine TC, HDL-C, LDL-C, and other cholesterol sub-fractions and blood lipoprotein components (e.g., VLDL-C and TG). Accordingly, the assays, methods, reagents, kits, devices, and systems disclosed herein provide improvements over the art.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE DRAWINGS

FIG. 4A: LDL-C results (showing the difference in absorbance measured at 6 minutes minus the absorbance measured at 2 minutes).

FIG. 4C: TC results, absorbance measured at 10 minutes.

$$\text{VLDL-C} = 0.152 \times \text{TC} + 0.15 \times \text{TG} - 0.549 \times \text{HDL-C} + 0.0015 \times (\text{TG} - 192) \times (\text{TC} - 188) - 2.62$$

Figure 6:
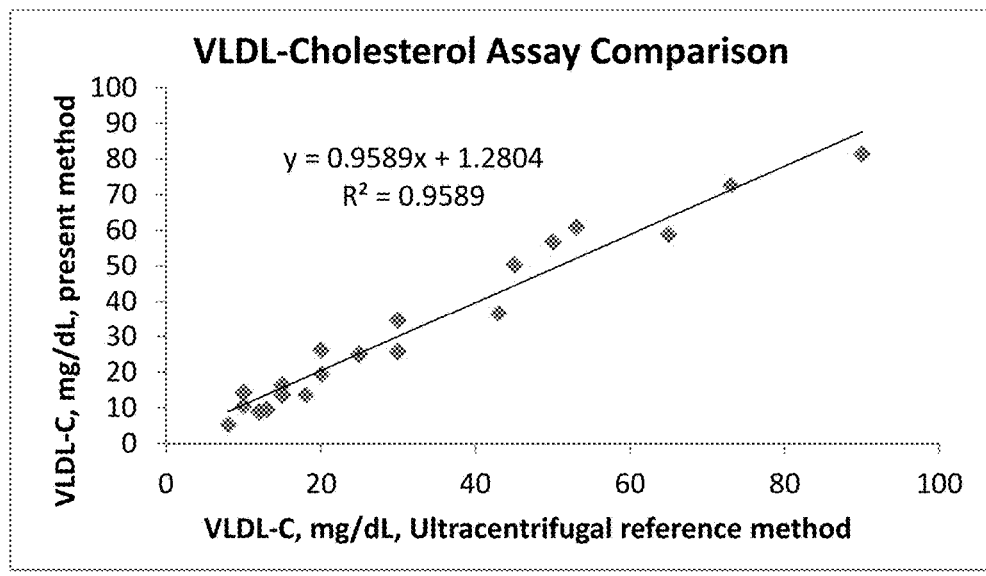
FIG. 6 shows comparisons of VLDL-C values, where the VLDL-C values obtained from prior art (ultracentrifugation) methods are plotted along the vertical axis, and VLDL-C values obtained from calculations based on HDL-C, TC, and TG measurements as disclosed herein. R squared ($R^2$) and other values indicating the goodness of fit are shown in the figures. For the results of the measurements shown in FIG. 6, VLDL-C was best calculated by the relationship.

(where "×" indicates multiplication). As indicated in FIG. 6, for the 20 data points shown in the figure, the VLDL-C values calculated according to the methods disclosed herein, i.e., by the equation above, agreed very well with the VLDL-C values obtained by ultracentrifugation methods (R squared of 0.959).

DETAILED DESCRIPTION

Applicants have found that very accurate and precise values for TC, LDL-C and HDL-C can be obtained in a single assay for cholesterol using kinetic measurements. Assays as disclosed herein may use a lipase, cholesterol esterase, cholesterol oxidase and a peroxidase to form a colored product measurable by spectrophotometry. In the assays disclosed herein, color formed from all the cholesterol-containing species is directly proportional to the quantity of cholesterol converted.

Description and disclosure of examples of reagents, assays, methods, kits, devices, and systems which may be used as disclosed herein may be found, for example, in U.S. Pat. No. 8,088,593; U.S. application Ser. No. 13/244,947; U.S. Application Ser. No. 61/673,037; U.S. Application Ser. No. 61/673,245; U.S. Application Ser. No. 61/675,758; U.S. Application Ser. No. 61/675,811; U.S. Application Ser. No. 61/676,178; U.S. Application Ser. No. 61/697,797; U.S. Application Ser. No. 61/705,552; and U.S. Application Ser. No. 61/706,753; the disclosures of which patent and patent applications are all hereby incorporated by reference in their entireties.

Definitions

Before the present formulations and methods of use are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the assays, reagents, methods, devices, and systems disclosed herein are not limited to the specific embodiments described herein.

It must be noted that, as used in the specification and the appended claims, the singular forms "a," "an" and "the" include plural referents unless the context clearly dictates otherwise. Thus, for example, reference to "a surfactant" refers to a single surfactant or mixtures of different surfactants, and the like.

In this specification and in the claims that follow, reference will be made to a number of terms, which shall be defined to have the following meanings:

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, optionally greater than about 30%, optionally greater than about 40%, optionally greater than about 50% as a function of the reference value or comparator value.

As used herein, the terms "zwitterionic" and "dipolar" each refer to molecules having charged groups of opposite polarity.

As used herein, the term "amphiphilic" refers to a compound or compounds having both hydrophobic and hydrophilic properties; typically, an amphiphilic molecule has a hydrophobic portion and also has a hydrophilic portion. A hydrophobic portion of a molecule may be a nonpolar portion, relatively water-insoluble portion, such as a hydrocarbon chain portion. A hydrophilic portion of a molecule may be a polar, relatively water soluble portion, and may include an acidic or basic moiety capable of gaining or losing a charge in water solution. Surfactants are typically amphiphilic compounds. Exemplary commercially available amphiphilic compounds include Triton™ surfactants, polyethylenesorbitans such as the TWEEN® compounds, and poloxamers (e.g., ethylene oxide/propylene oxide block copolymers) such as Pluronics® compounds.

As used herein, a "surfactant" is a compound effective to reduce the surface tension of a liquid, such as water. A surfactant is typically an amphiphilic compound, possessing both hydrophilic and hydrophobic properties, and may be effective to aid in the solubilization of other compounds. A surfactant may be, e.g., a hydrophilic surfactant, a lipophilic surfactant, or other compound, or mixtures thereof. Some surfactants comprise salts of long-chain aliphatic bases or acids, or hydrophilic moieties such as sugars. Surfactants include anionic, cationic, zwitterionic, and non-ionic compounds (where the term "non-ionic" refers to a molecule that does not ionize in solution, i.e., is "ionically" inert). For example, surfactants useful in the reagents, assays, methods, kits, and for use in the devices and systems disclosed herein include, for example, Tergitol™ nonionic surfactants and Dowfax™ anionic surfactants (Dow Chemical Company, Midland, Mich. 48642); polysorbates (polyoxyethylenesorbitans), e.g., polysorbate 20, polysorbate 80, e.g., sold as TWEEN® surfactants (ICI Americas, New Jersey, 08807); poloxamers (e.g., ethylene oxide/propylene oxide block copolymers) such as Pluronics® compounds (BASF, Florham Park, N.J); polyethylene glycols and derivatives thereof, including Triton™ surfactants (e.g., Triton™ X-100; Dow Chemical Company, Midland, Mich. 48642) and other polyethylene glycols, including PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, sucrose monostearate, sucrose monolaurate, sucrose monopalmitate, PEG 10-100 nonyl phenol series, PEG 15-100 octyl phenol series, and poloxamers; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; phosphocholines, such as n-dodecylphosphocholine, (DDPC); sodium dodecyl sulfate (SDS); n-lauryl sarcosine; n-dodecyl-N,N-dimethylamine-N-oxide (LADO); n-dodecyl-β-D-maltoside (DDM); decyl maltoside (DM), n-dodecyl-N,N-dimethylamine N-oxide (LADO); n-decyl-N,N-dimethylamine-N-oxide, 1,2-diheptanoyl-sn-glycero-3-phosphocholine (DHPC); 1,2-dilauroyl-sn-glycero-3-phosphocholine (DLPC); 2-methacryloyloxyethyl phosphorylcholine (MPC); 1-oleoyl-2-hydroxy-sn-glycero-3-[phospho-RAC-(1-glycerol)] (LOPC); 1-palmitoyl-2-hydroxy-sn-glycero-3-[phospho-RAC-(1-glycerol)] (LLPG); 3-[(3-cholamidopropyl) dimethylammonio]-1-propanesulfonate (CHAPS); n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Hexadecyl-N,N-dimethyl-3-ammonio-1-propanesulfonate; Tetradecanoylamidopropyl-dimethylammonio-propanesulfonate; Hexadedecanoylamidopropyl-dimethylammonio-propanesulfonate; 4-n-Octylbenzoylamido-propyl-dimethylammonio Sulfobetaine; a Poly(maleic anhydride-alt-1-tetradecene), 3-(dimethylamino)-1-propylamine derivative; a nonyl phenoxylpolyethoxylethanol (NP40) surfactant; alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins, including lecithin, lysolecithin, phosphatidylcholine, phosphatidylethanolamine, phosphatidylglycerol, phosphatidic acid, phosphatidylserine; lysolecithins and hydrogenated lysolecithins; phospholipids and derivatives thereof; lysophospholipids and derivatives thereof, including lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof; alkylmaltosides; alkylthioglucosides; lauryl macrogolglycerides; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and combinations thereof.

As used herein, the term "solubilizing" refers to dissolving a molecule in a solution.

The term "lipoprotein solubilization agent" as used herein refers to agents that aid in maintaining lipoprotein particles in solution. Amphiphilic compounds such as surfactants may be suitable for use as lipoprotein solubilization agents in the reagents, assays, methods, and kits disclosed herein, and in the devices and systems for the practice of such methods.

As used herein, a "colorant" is a compound (which may act alone or with other compounds) that is useful to alter an optical property of a solution, or to provide a new optical property to a solution. For example, a colorant may be may be a dye, a chromophore, a chromogenic compound, a chemiluminescent compound, a fluorescent compound, a fluorogenic compound (such as, e.g., Amplex red), a nanoparticle such as a quantum dot, or other element or compound which alters the optical properties of a solution. For example, a colorant may act, or may participate in a reaction to, alter an optical property of a solution to which it is added, or to provide or produce a luminescent, fluorescent, or other optically active product in the solution. An optical property of a solution may be, e.g., the color of a solution; the absorbance of a solution to a particular wavelength, range of wavelengths, or combination of wavelengths, of light; the amount or peak wavelength of luminescence or fluorescence of a solution; the turbidity of a solution; or any other property of a solution affecting the reflection, or absorbance of light by a solution. As used herein, the term "colorant" also refers to a compound or result of a reaction that may alter the turbidity of a solution or the clarity of a solution. A colorant may act, or may participate in a reaction to, change the absorbance of light through a solution to which the colorant is added. It will be understood that "a colorant" may refer to a one molecule or class of molecules, or may refer to a pair of molecules or classes of molecules that may together act to alter an optical property of a solution, or may refer to multiple molecules or classes of molecules that may together act to alter an optical property of a solution.

A peroxidase that participates in a reaction with its substrate(s) to form a colored product is a colorant, as are substrates of the peroxidase. For example, the colorant horseradish peroxidase (HRP) participates in a reaction with any one or more of several molecules effective to change the optical properties of a solution to which the HRP is added (e.g., by changing the color, the absorbance of light through a solution to which the HRP is added, and/or other optical properties of the solution). For example, HRP may react with an aniline-containing compound such as N-Ethyl-N-(2-hydroxy-3-sulfopropyl)-3,5-dimethoxyaniline (ALPS), or with an aminoantipyrene compound such as 4-aminoantipyrene or with phenolic compounds. Thus, for example, a peroxidase (e.g., HRP, myeloperoxidase, or other peroxidase), an aniline-containing compound, and an aminoantipyrene may all be termed "colorants." In further examples, HRP may react with a benzidine-containing compound (e.g., with diaminobenzidine (DAB); tetramethylbenzidine (TMB); 2,2'-azino-bis(3-ethylbenzothiazoline-6-sulphonic acid) (DABS); 3-dimethylaminobenzoic acid (DMAB); hydroquinone; o-tolidine; o-phenylenediamine; o-chlorophenol; p-hydroxy-benzenesulfonate; p-anisidine; a Trinder reagent (such as 4-aminoantipyrene, methylbenzothiazolinonehydrazone (MBTH), or other compound for producing a Trinder dye); and derivatives and related compounds) to form a colored product. HRP or other peroxidase may also react with other compounds to form a chemiluminescent product; for example, HRP or other peroxidase may react with luminol to form a chemiluminescent product (other molecules may be present, and may enhance such reactions; for example, HRP-mediated production of luminescent products from luminol is enhanced in the presence of 4-iodophenol). Other colorants include, for example, alkaline phosphatase; resazurin (7-Hydroxy-3H-phenoxazin-3-one 10-oxide); 10-acetyl-3,7-dihydroxyphenoxazine (Amplex Red) and similar compounds (e.g., Amplex UltraRed (A36006 from Life Technologies, Carlsbad, Calif. 92008); resorufin compounds (e.g., 7-ethoxyresorufin); dyes such as e.g., fluorescein, calcein, rhodamine, and ethidium dyes; N-methyl-4-hydrazino-7-nitrobenzofurazan; acridinium (acridine-9-carboxylic acid) esters and compounds which react with these compounds to alter an optical property of a solution; phenols and phenol derivatives (e.g., p-iodophenol and p-phenylphenol); luminescent amines, including amine adducts (e.g., as may be derived from copper cyanide), and other molecules. It will be understood that other enzymes and reactants may be used to form colored products, or to detect cholesterol in a blood sample.

As used herein, the terms "product formation," "colored product," "colored product formation," and the like are used to refer to the act of, and the products that result from, addition of a colorant to a solution. For example, addition of a colorant to a solution may result in a reaction effective to alter an optical property of the solution. Such a reaction may result in the formation of molecules originally not present in the solution, or may result in the aggregation of molecules or compounds previously in the solution, or may result in the degradation or other alteration of molecules or compounds previously in the solution, effective to alter the color, absorbance, and/or other optical properties of a solution to which a colorant is added.

A sample, as used herein, is a biological specimen obtained from a subject, and may be, without limitation, a blood sample, a urine sample, a throat or cheek swab, a tissue sample, a sample of cerebrospinal fluid, or other sample which may be obtained from a subject. As used herein, the term "a sample" includes a complete biological specimen and includes a portion or an aliquot of a biological specimen, such as a blood draw taken from a subject. A sample is typically obtained for analysis, e.g., for determination of one or more biologically relevant attributes such as, e.g., total cholesterol and/or other lipoprotein measurement; blood triglyceride (TG) level; hematocrit; pH, glucose level; uric acid level; salt concentration (e.g., of a cation and/or anion which makes up a salt); blood iron content; erythrocyte sedimentation rate (ESR); a cytometric measurement (e.g., cell size, cell density, cell morphology, cell type, detection of cell surface and/or intracellular markers and attributes, etc.); a chemical measurement including a measurement of the presence of and/or concentration of a vitamin, a protein, a metabolite of a protein or small molecule, and other measurements of blood, urine, tissue, or other biological sample.

A sample, such as a blood sample, or a portion of a blood sample, may be of any suitable size or volume, and is optionally of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, "lipoproteins" and "lipoprotein particles" include, without limitation, chylomicrons, very low density lipoprotein (VLDL), low density lipoprotein (LDL), and high density lipoprotein (HDL). Lipoproteins contain, among their multiple constituents, triglycerides (TG) and cholesterol, including cholesterol esters and other forms of cholesterol. The cholesterol (in all its forms) within or attached to lipoproteins is termed VLDL-C, LDL-C, and HDL-C, respectively. The total cholesterol (TC) of a blood sample includes the cholesterol sub-fractions VLDL-C, LDL-C, and HDL-C.

As used herein, "lipoprotein precipitation," "precipitation of lipoproteins," and similar terms refer to aggregation of lipoproteins (e.g., by exposure to divalent cations such as magnesium ions in the presence of negatively charged polymers, e.g., negatively charged polysaccharides such as dextran sulfate) and may also refer to centrifugation or other action to further separate lipoproteins from other blood components. Substantial precipitation of lipoproteins may occur when a large fraction, such greater than about 75%, or greater than about 80%, or greater than about 85%, or greater than about 90%, or greater than about 95%, or greater than about 99%, of the lipoproteins in a sample of blood are aggregated or precipitated.

As used herein, the term "lipoprotein interactant" refers to a compound, or pair, or group of compounds, which may act to aggregate and/or precipitate lipoproteins from a solution. It will be understood, however, that the term "lipoprotein interactant" is used herein as an identifier, and that the use or inclusion of such compounds need not require precipitation of lipoproteins in a solution or during an assay in which lipoprotein interactants may be present. An exemplary form of interaction with a lipoprotein is mediated by cations, such as magnesium and other divalent cations, where a negatively charged polymer, such as a negatively charged polysaccharide (e.g., a dextran sulfate) associates with a lipoprotein via the charged cations. Thus, such cations as, for example, magnesium (typically in the form of $MgCl_2$) may be termed "lipoprotein interactants." Other lipoprotein interactants include, without limitation, dextrans, cyclodextrins, phosphotungstic acid, phosphotungstic acid salts (e.g., sodium phosphotungstate, including sodium phosphotungstate with magnesium chloride), polyvinyl sulfate, heparins, heparin with manganese chloride, polyethylene glycols (e.g., polyethylene glycol (PEG) 6000), and antibodies (such as, for example, anti-apolipoprotein-B-specific monoclonal antibodies). Antibodies are typically used with centrifugation methods in lipoprotein assays.

Dextrans for use in methods and reagents as described herein may be obtained, for example, as dextran sulfate. Cyclodextrins, such as α-cyclodextrins, for use in methods and reagents as described herein may be obtained, for example, as cyclodextrin sulfate. In some prior art methods, lipoproteins may be precipitated from a blood sample by relatively low concentrations of dextran sulfate and relatively high concentrations of magnesium chloride (e.g., 0.182 μM dextran sulfate and 32 mM $MgCl_2$ as described by Kimberly et al. (*Clinical Chemistry* 45(10):18803-1812 (1999)).

As used herein, the term "dextran" refers to any form of a complex, branched glucan (that is, polysaccharide made of many glucose molecules) composed of polysaccharide chains of varying lengths. Linkages between glucose molecules along straight lengths of polysaccharide chains (e.g., between branches) are typically α-1,6 glycosidic linkages, while branching linkages between glucose molecules are typically α-1,3 glycosidic linkages. The sizes and molecular weights of dextrans varies widely; for example, dextran polysaccharide chains may have widely varying lengths, and dextrans exhibit great variation in molecular weight (e.g., from about 3 kilodaltons (kD) to about 2000 kD or more). As used herein, the term "dextran" includes dextran esters and salts, such as, e.g., dextran sulfate salts, dextran acetate salts, dextran propionate salts, dextran succinate salts, and other dextran salts.

It will be understood that a dextran molecule may be found, or may be provided, in a heterogenous mixture containing different dextran molecules each of which may have a different structure and/or a different molecular weight than other dextran molecules in a dextran composition such as a bulk composition of dextran. As used herein, the terms "dextran molecular weight," "molecular weight of a dextran," and similar terms refer to the average molecular weight of dextran molecules in a bulk composition of dextran, and does not suggest that all, or even most, dextran molecules in a bulk composition of dextran have the particular molecular weight identified as the "dextran molecular weight." Thus, it will be understood that the molecular weight of a dextran refers to an average value attributed to a bulk composition comprising a heterogenous mixture of dextran molecules which may vary in their weight and structure.

As used herein, the term "low molecular weight dextran" refers to a dextran in which the dextran molecular weight is less than about 100 kilodaltons (kD), and is typically less than about 75 kD; in embodiments, a low molecular weight dextran may have a molecular weight of between about 25 kD and about 75 kD, or between about 40 kD and about 60 kD. In embodiments, a low molecular weight dextran may have a molecular weight of about 50 kD.

As used herein, the term "cyclodextrin" refers to any cyclic polysaccharide, e.g., a cyclic compound made up of sugar molecules. The number of sugar molecules in the ring of a cyclodextrin may vary; for example, cyclodextrins having six sugars in a ring are termed α-cyclodextrins; those having seven-membered rings are termed β-cyclodextrins; and cyclodextrins having eight sugar molecules in a ring are termed γ-cyclodextrins.

As used herein, a negatively charged polymer is any organic molecule containing repeating units and having a negative charge in water solution at near neutral pH (e.g., pH between about pH 5 and about pH 9, optionally between about pH 6 and about pH 8). For example, polyvinyl sulfate is a negatively charged polymer. Other negatively charged polymers include negatively charged polysaccharides, including heparins and dextran esters.

Cholesterol may be measured in the blood of a subject, such as a human subject. The cholesterol measured in a blood sample may be referred to as comprising cholesterol of one or more cholesterol sub-fraction. As used herein, the term "total cholesterol" and its acronym "TC" is used to indicate the total amount of cholesterol in a sample. Where the amount of cholesterol in a blood sample is discussed, and where not otherwise indicated, the term "cholesterol" refers to "total cholesterol." Cholesterol may be found in many forms in the blood of a subject (e.g., a human subject); for example, cholesterol may be found in the blood in chylomicrons, in VLDL, in LDL, and/or in HDL. Each of chylomicrons, VLDL, LDL, and HDL may be termed a cholesterol sub-fraction. The sum of the amounts of cholesterol present in the chylomicron, VLDL, LDL, and HDL sub-fractions makes up the total cholesterol in a sample of blood obtained from a subject.

The total amount of cholesterol, and the amounts of cholesterol in individual, and in each, cholesterol sub-fraction, may be measured by a variety of means know in the art, and by the novel methods and means disclosed herein. As used herein, the term "cholesterol measurement data" refers to the data resulting from measurements of cholesterol in a sample, and may refer to measurements of TC, VLDL-C, LDL-C, HDL-C, chylomicron cholesterol, and combinations thereof, without limitation. For example, as disclosed herein, cholesterol may be measured by any suitable means, including amperommetry, voltammetry, or other means, including by measuring an optical property of a blood sample, such as a blood sample following addition of a reagent or reagents according to methods and assays disclosed herein. For example, as disclosed herein, cholesterol may be measured by measuring absorbance in a blood sample, e.g., in a blood sample following addition of a reagent or reagents according to methods and assays disclosed herein. In embodiments, cholesterol measurement data comprises data obtained by measuring absorbance using a spectrophotometer. In embodiments, cholesterol measurement data comprises data obtained by measuring $\Delta A$ using a spectrophotometer, where $\Delta A$ is the difference between absorbance measured at two wavelengths, such as, e.g., between about 560 nm and about 700 nm. Thus, for example, cholesterol measurement data may be obtained by measuring $\Delta A$ using a spectrophotometer, by measuring absorbance at a wavelength of about 560 nm and at a wavelength of about 700 nm, and calculating or otherwise obtaining the difference between these absorbance measurements.

The term "absorbance" is used herein according to its usual and customary meaning in the art, and refers to the optical property of a solution (e.g., a sample) related to the ratio of the amount of optical (e.g., electromagnetic) radiation falling upon a solution to the amount of optical radiation transmitted through the solution (e.g., the sample).

Absorbance may be measured by measuring the amount of light absorbed during passage through a medium, by measuring the amount of light that passes through a medium, or by other method known in the art. Transmittance (T) is typically defined as the ratio of the amount of light passing through a sample to the amount of light passing through a control (e.g., a blank), where the amount of light is typically measured by light intensity. The amount of light that fails to pass through the medium is thus 1−T. The absorbance A is typically defined as the negative $\log_{10}$ of T. Thus, absorbance and transmittance are measured together, as determination of one of these values allows determination of the other value. Thus, as used herein, "absorbance" also indicates and refers to "transmittance" as determination of absorbance allows for the determination of transmittance as well.

As used herein, absorbance (and transmittance) may be measured within a particular range of wavelengths, or at a particular wavelength, or at multiple particular wavelengths. Absorbance measured at a particular wavelength may be obtained by measurements within a range of wavelengths centered around that particular wavelength. For example, absorbance at 560 nm may be obtained by measuring absorbance between wavelengths of about 530 nm to about 590 nm; by measuring absorbance between wavelengths of about 540 nm to about 580 nm; optionally by measuring absorbance between wavelengths of about 550 nm to about 570 nm; or between other wavelengths greater and lesser than 560 nm. Similarly, absorbance at 700 nm may be obtained by measuring absorbance between wavelengths of about 670 nm to about 730 nm; by measuring absorbance between wavelengths of about 680 nm to about 720 nm; optionally by measuring absorbance between wavelengths of about 690 nm to about 710 nm; or between other wavelengths greater and lesser than 700 nm. Absorbance was measured using a spectrophotometer in the Examples disclosed herein.

As used herein, the term "ΔA" refers to the difference in absorbance measured at a first wavelength and absorbance measured at a second wavelength; for example, a first wavelength may be about 560 nm and a second wavelength may be about 700 nm. For example, ΔA may be measured by the difference in absorbance measured at a wavelength of about 560 nm and at a wavelength of about 700 nm, and calculating or otherwise obtaining the difference between these absorbance measurements. Thus, for example, such a ΔA measured at 560 nm and 700 nm may be termed "ΔA (560-700 nm)."

As used herein, the term "spectrophotometer" refers to a device configured for, and effective to, measure optical intensity within a particular range of wavelengths, or at a particular wavelength, or at multiple particular wavelengths. A spectrophotometer may be effective to measure absorbance in a sample. A spectrophotometer may be effective to measure light emitted from a sample (e.g., fluorescence and/or luminescence). A spectrophotometer may be effective to measure absorbance in a sample and to measure light emitted from a sample.

As used herein the term "spectrophotometry" refers to the making of measurements using a spectrophotometer; e.g., to the making of optical measurements within a particular range of wavelengths, or at a particular wavelength, or at multiple particular wavelengths.

As used herein, the term "optical detector" and means for measuring an optical property (e.g., of a colored solution) refer to any suitable optical means, optical device, photodetector, and optical device element for detecting electromagnetic radiation (e.g., light of any wavelength). For example, an optical detector, and optical detection means, may be used to detect absorbance, transmittance, turbidity, luminescence (including chemiluminescence), fluorescence and/or other optical signal. Optical detectors include, but are not limited to, imaging devices. Optical means, optical devices, photodetectors, and optical device elements include, but are not limited to, electronic detectors such as digital cameras, charge coupled devices (CCDs, including super-cooled CCDs), photodiodes (including, e.g., pin diodes and avalanche photodiodes), photomultipliers, photo-totubes, photon counting detector, arrays of photodiodes (including, e.g., pin diode arrays and avalanche photodiode arrays), arrays of charge coupled devices (including supercooled CCD arrays), arrays of photodiodes, arrays of photomultipliers, arrays of phototubes, arrays of photon counting detectors, and other detection devices and detection elements. In some embodiments a pin diode or other element may be coupled to an amplifier.

In some embodiments, an optical detector may include a camera (e.g., a digital camera). A camera may include a lens, or may operate without a lens. In some instances, cameras may include CCDs, may use complementary metal-oxide semiconductor (CMOS) elements, may be lensless cameras, microlens-array cameras, open-source cameras (including, e.g., a Frankencamera as described by Levoy, "Experimental Platforms for Computational Photography," *IEEE Computer Graphics and Applications*, Vol. 30, No. 5, September/October, 2010, pp. 81-87) and may use any visual detection technology known or later developed in the art. Cameras may acquire conventional and/or non-conventional images, e.g. holographic images, tomographic images, interferometric images, Fourier-transformed spectra, any or all of which may be interpreted with or without the aid of computational methods. Cameras may include one or more feature that may focus the camera during use, or may capture images that can be later focused. In some embodiments, imaging devices may employ two-dimensional (2-D) imaging, three-dimensional (3-D) imaging, and/or four-dimensional (4-D) imaging (incorporating changes over time). Imaging devices may capture static images. Optical schemes used to achieve 3-D and 4-D imaging may be one or more of the several known to those skilled in the art, e.g. structured illumination microscopy (SLM), digital holographic microscopy (DHM), confocal microscopy, light field microscopy etc. Static images may be captured at one or more point in time. Imaging devices may capture video and/or dynamic images. Video images may be captured continuously over a single period, or may be captured over one or more periods of time. An imaging device may collect signal from an optical system which scans a target (e.g., a sample used for an assay) in arbitrary scan patterns (e.g., in a raster scan).

An optical detector, and optical detection means, include without limitation, a microscope, and means for optical detection may include microscopy, visual inspection, via photographic film, or may include the use of electronic detectors such as digital cameras, charge coupled devices (CCDs), super-cooled CCD arrays, phototubes, photodetectors, and other detection devices known in the art, and as disclosed herein. An optical detector, and optical detection means, may include an optical fiber or a plurality of optical fibers (e.g., fiber optic cables) which may, for example, be functionally connected to a CCD detector or to a PMT array. A fiber optic bundle may comprise discrete fibers and/or many small fibers fused together to form a solid bundle.

An optical detector may include a light source, such as an electric bulb, incandescent bulb, electroluminescent lamp, laser, laser diode, light emitting diode (LED), gas discharge lamp, high-intensity discharge lamp, a chemiluminescent light source, a bioluminescent light source, a phosphorescent light source, a fluorescent light source, and natural sunlight. In embodiments, e.g., where chemiluminesence is to be detected, light may be produced by the assay chemistry. In embodiments, a light source can illuminate a component in order to assist with detecting the results. For example, a light source can illuminate a solution in assay in order to detect the results of the assay. For example, an assay can be a fluorescence assay or an absorbance assay, as are commonly used with nucleic acid assays. A detector may comprise optical elements effective to deliver light from a light source to an assay or assay chamber. Such an optical element may include, without limitation, for example, a lens, a mirror (e.g., a scanning or galvano-mirror), a prism, a fiber optic fiber or bundle of fibers, a light guide (e.g., a liquid light guide), and/or other optical element. An optical detector may include such optical elements, where such optical elements are disposed effective to deliver light to a detector. For example, an optical detector may be configured to detect selected wavelengths or ranges of wavelengths of electromagnetic radiation. An optical detector may be configured to move over, or to view portions of, a sample. An optical detector may include a mirror, a motor, a piezoelectric element, or other element effective to allow detection of light from different portions of a target location at different times, e.g., to scan a sample.

An optical detector may be used to detect one or more optical signal. For example, a detector may be used to detect the presence of, or progress of a reaction providing luminescence. A detector may be used to detect a reaction providing one or more of fluorescence, chemiluminscence, photoluminescence, electroluminescence, sonoluminescence, absorbance, turbidity, optical-rotary-dispersion (ORD), circular dichroism (CD), or polarization. An optical detector may be able to detect optical signals relating to color intensity and phase or spatial or temporal gradients thereof.

As used herein, a means for communicating information from said device to a computer or other external device, and a channel for communicating information to a computer or other external device, without limitation refers to a computer network, a telephone, a telephone network, and a device configured to display information communicated from said device. In embodiments, a means for communicating information, and a channel for communicating information include direct links using wires (including twisted pair, coaxial, ribbon, and other cables), wireless means and wireless technology (e.g., Bluetooth technology or RTM (retransmission mode) technology). Communicating means and channels for communication include any suitable communication method, including a dial-up wired connection with a modem, a direct link using a wire, a wireless connection including infrared, cellular, wimax, wifi, satellite, pager, general packet radio service (GPRS), local data transport system (such as, e.g., ethernet or token ring over a local area network (LAN) or other network).

An external device to be communicated with may be any device capable of receiving such a communication. For example, an external device may be a networked device, including a server, a personal computer, a laptop computer, a tablet, a mobile device, a "dumb" cell phone, a satellite phone, a smart phone (e.g., iPhone®, Android™, Blackberry®, Palm, Symbian, Windows®), a personal digital assistant (PDA), a pager or any other device. In embodiments, an external device may be a diagnostic device. In some embodiments where an external device comprises a diagnostic device, the relationship between devices and systems disclosed herein and an external device may comprise a master-slave relationship, a peer-to-peer relationship, or a distributed relationship.

As used herein, the term "lipase" refers to a class of enzymes that catalyze reactions with a lipid as a part of the reaction substrate. Lipases may catalyze reactions such as hydrolysis or other reactions. For example, a lipase may catalyze a reaction where a cholesterol ester is metabolized to cholesterol and a fatty acid.

As used herein, the term "cholesterol esterase" refers to an enzyme effective to catalyze a reaction that removes or alters an ester bond, such as a carboxylic acid ester, of a cholesterol molecule or cholesterol moiety of a cholesterol-containing molecule. Cholesterol esterases (also known as "sterol esterases" and as "bile lipases") typically catalyze a reaction in which a steryl ester combines with water to form a sterol and a fatty acid. Cholesterol esterases are common, and may be found in single-cell and in multi-cellular organisms; many commercially useful cholesterol esterases are bacterial cholesterol esterases, although cholesterol esterases from other sources are known and are useful as well. For example, a useful cholesterol esterase may be a bacterial cholesterol esterase, such as a cholesterol esterase obtained from Gram-negative bacteria, including a cholesterol esterase from a *Pseudomonas* species.

As used herein, the term "cholesterol oxidase" refers to an enzyme effective to catalyze a reaction in which a cholesterol molecule or a cholesterol moiety of a cholesterol-containing molecule combines with oxygen to form an oxidized cholesterol moiety such as cholest-4-en-3-one (also forming hydrogen peroxide). Many cholesterol oxidases are bacterial cholesterol oxidases. For example, a useful cholesterol oxidase may be a cholesterol oxidase, such as may be obtained from Gram-negative bacteria, including a cholesterol oxidase from a *Pseudomonas* species.

As used herein, a "buffer" is a compound or group of compounds which, in solution, tend to maintain the pH of the solution at or near a particular value. For example, phosphate salts may be used as buffers. Phosphate salts include $NaH_2PO_4$, $Na_2HPO_4$, and $Na_3PO_4$. Other buffers are also suitable for use in the reagents, assays and methods disclosed herein, including without limitation citrate, ammonium, acetate, carbonate, tris(hydroxymethyl)aminomethane (TRIS), 3-(N-morpholino) propanesulfonic acid (MOPS), 3-morpholino-2-hydroxypropanesulfonic acid (MOPSO), 2-(N-morpholino)ethanesulfonic acid (IVIES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yl] amino]ethanesulfonic acid (TES), 4-(2-hydroxyethyl)-1-piperazine ethanesulfonic acid (HEPES), acetamidoglycine, tricine (N-(2-Hydroxy-1,1-bis(hydroxymethyl)ethyl)glycine), glycinamide, bicine (2-(Bis(2-hydroxyethyl)amino) acetic acid), and other buffers. Any buffer may be used as long as it buffers a water solution at the desired pH and is otherwise compatible with the assays and methods disclosed herein. In embodiments, a buffer may be used to buffer the pH of a solution in a pH range of near neutral pH to slightly acidic pH, for example, from about pH 5 to about pH 9, or between about pH 6 to about pH 8, or between about pH 6.8 to about pH 7.8, and in embodiments, to a pH of about pH 7 or of about pH 7.4.

The novel methods and assays disclosed herein make use of Applicants' finding that cholesterol sub-species are converted to the measured product at distinct rates. Accordingly, HDL-C is converted very rapidly to product, while LDL-C is converted to product more slowly than HDL-C is converted to product and VLDL-C and chylomicrons are converted even more slowly. Complete conversion of total cholesterol to product is even slower than the conversion of HDL-C or LDL-C to product. Such differences in rates of conversion to product allow the measurement of cholesterol from different lipoprotein species to be made in a single solution at different times, thus reducing the number of steps needed for such measurements, reducing possible errors and simplifying the procedures. In embodiments disclosed herein, "product" may be a colored product, such as, e.g., a colored product formed by a peroxidase such as horseradish peroxidase. By making measurements of colored product at, for example, (1) very early times (for example, 0-2 minutes), at somewhat later times (for example, 2-6 minutes) and at late time (for example, 10 minutes or later) the two most important cholesterol sub fractions (HDL-C and LDL-C) and total cholesterol (T-C) can be measured in a single assay. Importantly, since the assay is performed in a single reaction mixture, the ratios of cholesterol sub-fractions to total cholesterol are determined more accurately and precisely than would be expected by performing several different assays in different reaction mixtures. Additionally, assays and methods disclosed herein, being performed in a single reaction mixture, can significantly reduce the costs of cholesterol measurements as compared to the costs of prior methods and assays which require running three or more assays to obtain cholesterol sub-fraction and total cholesterol values.

Methods and assays disclosed herein make use of the differential rates at which each cholesterol-containing lipoprotein fractions are acted on by a lipase (e.g., a cholesterol esterase) and an oxidase (e.g., a cholesterol oxidase). The lipoproteins differ in the composition of the lipids they contain (e.g., lipids including triglycerides, cholesterol, cholesterol esters, and phospholipids) and in the apo-lipoproteins that help solubilize lipids for transport through blood. Lipoproteins are very heterogeneous but the fractions thought to be of most utility in assessing lipid status for clinical diagnostic purposes are sufficiently distinct in their physical and chemical properties, and have been distinguished in prior art methods by the rates at which they move under centrifugal force or when subject to electrophoretic separation.

In contrast to prior art methods, the assays and methods disclosed herein utilize, and the reagents disclosed herein provide, conditions in which HDL, LDL, and VLDL lipoproteins react with the assay chemistry at sufficiently different rates in the same solution without substantial precipitation so that each fraction can be measured in a single assay using multiple measurements at different times. Thus in one example of methods disclosed herein HDL-C is completely consumed by about two minutes while LDL-C requires about six minutes to be completely converted to measured product. By waiting somewhat longer (e.g., ten minutes, or longer) all the cholesterol in the sample is converted. According to the methods disclosed herein, total cholesterol can be estimated at the assay end-point by measuring the absorbance of the colored product. According to the methods disclosed herein, LDL-C can be measured by taking the rate of color production over a range of time (for example 2-6 minutes). During the earliest part of the reaction (e.g., 0-2 minutes) both HDL and LDL are being consumed; the contribution of HDL can be estimated using the LDL concentration measured within the assay (e.g., once the LDL concentration is known from measurements made with the assay). As disclosed herein, a method for doing the calculation has been established. The present methods thus allow the use of rate data alone to compute HLD-C and LDL-C and Total-C. LDL-C may be calculated from kinetic data taken from the middle part of the assay reaction (e.g., measurements taken at about 2 to 6 minutes after initiation of the assay) and HDL-C may be estimated from the early part (e.g., about 0 to 2 minutes after initiation of the assay) of the reaction allowing for the contribution of LDL.

Applicants have found that one aspect of assays disclosed herein involves setting up assay conditions (e.g., reagents, protocol and temperature) so that, in the same solution without substantial precipitation of lipoproteins, the kinetics of reactions converting HDL-C, LDL-C, chylomicrons, and VLDL-C to colored product proceed at significantly different rates while allowing essentially complete reaction of all lipoprotein species (e.g., HDL, LDL, and VLDL) before the end of the assay. The reagents and methods disclosed herein provide the conditions which allow the differentiation over time between different lipoprotein fractions in a single reaction mixture without substantial lipoprotein precipitation.

For example, under the conditions disclosed herein, the time course for HDL-C has a half-time estimated at less than one minute whereas the LDL-C conversion has a lag phase and an overall sigmoid shape centered on about three minutes. Under the conditions disclosed herein, the remaining lipoprotein cholesterol (chylomicrons and VLDL-C) reacts even more slowly (e.g., with a half-time of about five minutes or longer). These differences in half-time and reaction kinetics between different lipoprotein cholesterol species enable the de-convolution of the assay signal to that attributable to each species using a simple algorithm even though, for example, signal is being produced from more than one species during certain times during the assay. Thus, the methods disclosed herein allow rapid, convenient, and accurate determination of cholesterol in the major lipoprotein fractions.

In conventional prior art assays LDL and VLDL are precipitated by one of a variety of reagents. For example, dextran sulfate and magnesium ions can bridge the negatively charged lipoprotein particles so they aggregate to form, for example, LDL:$Mg^{2+}$:Dextran sulfate:$Mg^{2+}$:LDL complexes. Precipitate formation in such conventional assays requires particular concentrations of both reagents in the correct ratios. Precipitates in such conventional assays can then be removed by centrifugation or filtration. Other LDL and VLDL precipitating reagents are known such as phosphotungstic acid, polyvinyl sulfate, Heparin with Manganese Chloride, Polyethylene glycol (PEG) 6000, Sodium Phosphotungstate with Magnesium Chloride and anti-apo-lipoprotein-B-specific monoclonal antibodies.

In contrast, reagent formulations for use in the assays and methods disclosed herein are designed to achieve the kinetic differentiation described above without requiring precipitation of any lipoproteins. In reagents disclosed herein, complex formation with magnesium and dextran sulfate is achieved in conditions in which essentially no precipitation of lipoproteins occurs. A variety of surfactants and other reagents such as α-cyclodextrin are suitable for use in keeping the lipoproteins soluble. The LDL and VLDL particle surfaces are modified in such a way as to restrict but not prevent access to LDL and VLDL cholesterol and cholesterol esters. The use of reagents and methods suitable for such modification of LDL and VLDL particle surfaces is effective to slow the formation of colored product from these lipoprotein species.

One exemplary reagent composition shown below in Table 3 uses a lower molecular weight dextran sulfate and a much higher magnesium ion concentration and ratio of magnesium ions to dextran sulfate as compared to prior art predicate methods. In the first step in the assay the concentrations of these ingredients are reduced to half due to addition of sample in both the present and predicate methods.

It will be understood that the particular ingredients and their amounts may vary in the reagents used in the practice of the methods disclosed herein. The reagent compositions shown in Table 3 provide one example of many possible reagents that are suitable for use in these methods. In general, the reagents will include cations, and the cations in reagents suitable for use in these methods will optionally be divalent cations, such as magnesium, manganese, calcium, barium, and other divalent cations. In embodiments of the reagents for use in the methods disclosed herein, the divalent cation concentration will be in the range of about 0.1 mM to about 20 mM, optionally between about 1 mM to about 10 mM, or optionally between about 2 mM and about 8 mM. In general, the reagents will include negatively charged polysaccharides, and the negatively charged polysaccharides in reagents suitable for use in these methods will optionally be dextran esters, such as dextran sulfate. In embodiments of the reagents for use in the methods disclosed herein, the amount of negatively charged polysaccharide (e.g., dextran sulfate) will be in the range of about 0.1 g/L to about 20 g/L, optionally between about 0.3 g/L to about 10 g/L, or optionally between about 0.5 g/L and about 5 g/L. In particular embodiments of reagents suitable for use in the methods disclosed herein, the negatively charged polysaccharides (e.g., dextran sulfate) will have molecular weights in the range of between about 10,000 to about 1,000,000, optionally in the range of between about 20,000 to about 500,000, optionally in the range of between about 25,000 to about 100,000, or optionally in the range of between about 30,000 to about 80,000. In particular embodiments of reagents suitable for use in the methods disclosed herein, the ratio of negatively charged polysaccharides (e.g., dextran sulfate) to divalent cations will be in the range of between about 0.001 to about 0.1, optionally in the range of between about 0.001 to about 0.05, optionally in the range of between about 0.002 to about 0.02, or optionally in the range of between about 0.003 to about 0.007.

In the examples disclosed herein, control ("predicate") measurements of cholesterol and cholesterol sub-fraction were made using Advia® chemistry and methods using an Advia® 1800 machine per the suggested instructions provided by the maker and supplier of the Advia® products, Siemens Healthcare Diagnostics (Tarrytown, N.Y. 10591 USA).

Accordingly, as described above, reagents, assays and methods providing negatively charged polysaccharides (such as dextran esters, e.g., dextran sulfate), optionally negatively charged cylodextrins (such as α-cyclodextrin sulfate), and cations (e.g., divalent cations such as magnesium) in the combined reagents with a blood sample during the assay after an initial time as discussed above, effective to provide different rates of degradation of cholesterol from different lipoprotein fractions so that measurement of the progress of the reaction at different times and/or during different time periods, as discussed above, is effective to measure and determine HDL-C, LDL-C, VLDL-C, and/or TC.

In alternative embodiments of the reagents, assays, and methods disclosed herein, a lipase (e.g., a cholesterol esterase), a dehydrogenase (e.g., a cholesterol dehdrogenase) and nicotine adenine dinucleotide (NAD) may be combined during an assay, e.g., a blood sample may be added to a reagent, or mixture of reagents, so that the blood sample, the lipase, the dehydrogenase, and NAD (e.g., in its oxidized form NAD$^+$) are all present in a solution effective that the lipase may act to release cholesterol from cholesterol esters in lipoproteins in the sample, and the dehydrogenase and nicotine adenine dinucleotide react effective to provide a reduced form of nicotine adenine dinucleotide (NADH) and cholest-4-en-3-one or other form of cholesterol, effective to provide a colored product (e.g., NADH) or other detectable product. In such alternative embodiments, similar amounts of negatively charged polysaccharides (such as dextran esters, e.g., dextran sulfate), optionally negatively charged cylodextrins (such as α-cyclodextrin), and cations (e.g., divalent cations such as magnesium) are present in the reagents and in the combined reagents during the assay after an initial time as discussed above, effective to provide different rates of degradation of cholesterol from different lipoprotein fractions so that measurement of the progress of the reaction at different times and/or during different time periods, as discussed above, is effective to measure and determine HDL-C, LDL-C, VLDL-C, and/or TC.

Thus, in such alternative embodiments, nicotine adenine dinucleotide is a colorant. The NADH may be detected by spectrophotometric or other means, as discussed above, effective that the levels of cholesterol may be detected and measured. For example, NADH may be detected and its levels determined by absorbance measurements at 340 nm or in a wavelength range centered about 340 nm. NADH may be excited by light having a wavelength of about 340 nm, and emits light with wavelengths of about 440 nm; thus NADH may be detected by excitation at about 340 nm and measuring emission at about 440 nm. Other methods for detecting and measuring NADH levels (e.g., to determine cholesterol levels in a blood sample) include measurement of NADH formation using redox sensitive molecules such as tetrazolium salts in the presence of a redox mediator such as diaphorase; amperometric methods; and luminogenic methods which consume NADH (e.g., using luciferase-mediated light production, such as by use of a bacterial luciferase).

It is to be understood that while the above disclosure has been described in conjunction with the specific embodiments thereof, that the description above as well as the examples that follow are intended to illustrate and not limit the scope of the invention. Other aspects, advantages and modifications within the scope of the invention will be apparent to those skilled in the art to which the invention pertains.

EXAMPLES

Example 1 Chemistry and Reagents

Figure 1A:
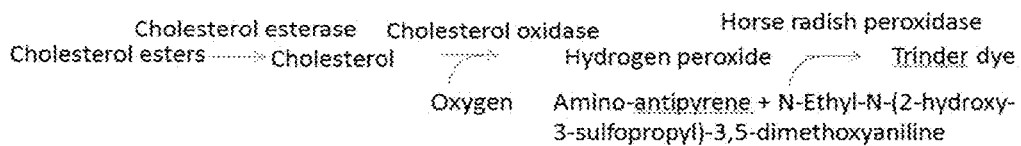
FIG. 1A shows an exemplary reaction scheme where cholesterol esters (e.g., as are found in lipoproteins in a sample of blood) may react with a cholesterol esterase to form cholesterol, which may react with a cholesterol oxidase and oxygen to form hydrogen peroxide. Hydrogen peroxide, in the presence of horseradish peroxidase and colorants such as an amino-antipyrene (e.g., 4-aminoantipyrene) and an aniline-containing compound (e.g., N-Ethyl-N-(2-hydroxy-3-sulfopropyl)-3,5-dimethoxyaniline) may react to form a colored product (e.g., a Trinder (e.g., quinoneimine) dye as indicated in the figure).

Cholesterol Assay Chemistry:

Assays disclosed herein may be used to form colored product from reactions with cholesterol and cholesterol derivatives (e.g., cholesterol esters) found in a blood sample. As shown in FIG. 1, cholesterol esters may react with a cholesterol esterase to provide free cholesterol. Free cholesterol may react with a cholesterol oxidase and oxygen to form hydrogen peroxide. The hydrogen peroxide formed in such a reaction may be used to quantify the amount of cholesterol in the sample. Hydrogen peroxide may react with a peroxidase to form a colored product, e.g., in the presence of a colorant, or by use of a colorant, and such a reaction can be detected and quantified. For example, hydrogen peroxide, in the presence of horseradish peroxidase and colorants such as aminoantipyrene compounds (e.g., 4-aminoantipyrene) and N-Ethyl-N-(2-hydroxy-3-sulfopropyl)-3,5-dimethoxyaniline, reacts to form a colored product (e.g., a Trinder (quinoneimine) dye as indicated in FIG. 1).

Cholesterol Assay Reagents:

Compositions for two exemplary reagents, AC and BC, are listed Tables 1 and 2 below. Reagent AC provides an example of a first reagent as disclosed herein, and Reagent BC provides an example of a second reagent as disclosed herein. Reagents AC and BC may have compositions as disclosed in Table 1A and 1B:

TABLE 1A

Composition of Reagent AC

| Component | Concentration |
| --- | --- |
| cyclodextrin (e.g., an α-, β-, or γ-cyclodextrin, as, e.g., a sulfate or phosphate) | 0.1 mM-10 mM |
| Negatively charged Dextran (50,000 MW) (e.g., as sulfate or phosphate) | 0.1 g/L-20 g/L |
| Magnesium salt (e.g., chloride, sulfate, acetate, carbonate, or other salt) | 1 mM-10 mM |
| 4-Aminoantipyrene | 1-5 mM |
| $Na_xPO_4$ (pH between about pH 6-pH 8, e.g., pH 7.4) | 20 mM-300 mM |

TABLE 1B

Composition of Reagent BC

| Component | Concentration |
| --- | --- |
| $Na_xPO_4$ (pH between about pH 6-pH 8, e.g., pH 7.4) | 10 mM-200 mM |
| Triton X-100 (octylphenol ethoxylate) | 0.01%-1% |
| Pluronic L64 (polyethylene glycol-polypropylene glycol co-block polymer) | 0.5 g/L-20 g/L |
| ALPS | 0.5 mM-20 mM |
| Horseradish Peroxidase | 0.5 kU/L-20 kU/L |
| Cholesterol Esterase from *Pseudomonas* sp. | 100 U/L-5000 U/L |
| Cholesterol Oxidase from *Pseudomonas* sp. | 0.25 kU/L-10 kU/L |

Where "ALPS" is N-Ethyl-N-(2-hydroxy-3-sulfopropyl)-3,5-dimethoxyaniline, and "$Na_xPO_4$" is $NaH_2PO_4$, $Na_2HPO_4$ and $Na_3PO_4$ in ratios effective to provide a pH of between about pH 6 to about pH 8.5; e.g., about pH 7.4.

For example, in particular embodiments, Reagents AC and BC may have the following compositions as listed in Tables 2A and 2B below:

TABLE 2A

Composition of Reagent AC

| Component | Concentration |
| --- | --- |
| α-cyclodextrin sulfate | 1 mM |
| Dextran Sulfate (50,000 MW) | 1 g/L |
| Magnesium Chloride | 4 mM |
| 4-Aminoantipyrene | 2.25 mM |
| $Na_xPO_4$ pH 7.4 | 100 mM |

TABLE 2B

Composition of Reagent B

| Component | Concentration |
| --- | --- |
| $Na_xPO_4$ pH 7.4 | 50 mM |
| Triton X-100 (octylphenol ethoxylate) | 0.06% |
| Pluronic L64 (polyethylene glycol-polypropylene glycol co-block polymer) | 3 g/L |
| ALPS | 3 mM |
| Horseradish Peroxidase | 3 kU/L |
| Cholesterol Esterase from *Pseudomonas* sp. | 750 U/L |
| Cholesterol Oxidase from *Pseudomonas* sp. | 1.5 kU/L |

Where "ALPS" is N-Ethyl-N-(2-hydroxy-3-sulfopropyl)-3,5-dimethoxyaniline, and "$Na_xPO_4$" is $NaH_2PO_4$, $Na_2HPO_4$ and $Na_3PO_4$ in ratios effective to provide a pH of between about pH 6 to about pH 8.5, e.g., about pH 7.4.

Table 3 provides a comparison of the amounts of dextran sulfate and magnesium chloride used in the novel reagents and assays disclosed herein, and the amounts of dextran sulfate and magnesium chloride used in prior art methods. In some prior art assays, dextran sulfate and magnesium chloride may be used to precipitate lipoproteins during assays for cholesterol and cholesterol-esters. As illustrated in Table 3, the present assays include different concentrations of dextran sulfate and magnesium chloride, so that there is substantially no precipitation of lipoproteins in the present assays.

TABLE 3

Comparison of some reagent-component concentrations.

| Interactant | Present Novel Assays (Concentration) | Predicate Method[‡] (Concentration) |
| --- | --- | --- |
| Dextran Sulfate | 1 g/L | 0.0091 g/L |
| Magnesium Chloride | 4 mM | 32 mM |

[‡]Predicate method: dextran sulfate-magnesium chloride method of Kimberly et al., *Clinical Chemistry* 45(10): 1803-1812 (1999).

Example 2—Cholesterol Assays

1) At 37° C., 304, sample (neat plasma or serum diluted 1:30 in water or phosphate buffered saline (PBS)) was combined with 204, Reagent AC in a well of a 384-well microplate reader (MTP).

2) The plate was shaken for 2 seconds at 1800 rpm.

3) The plate was incubated at 37° C. for 5 minutes.

4) 20 µL Reagent BC was added. The plate was shaken for 2 seconds at 1800 revolutions per minute (rpm).

5) The plate was incubated at 37° C. for 12 minutes in a spectrophotometer capable of reading absorbance at given time intervals.

6) Absorbance (A) was recorded at 560 nm and 700 nm every 30 seconds (an M5 spectrophotometer (Molecular Devices, Sunnyvale, Calif.) was used to make the measurements). Note that other intervals, including longer intervals, are also suitable.

Figure 2:
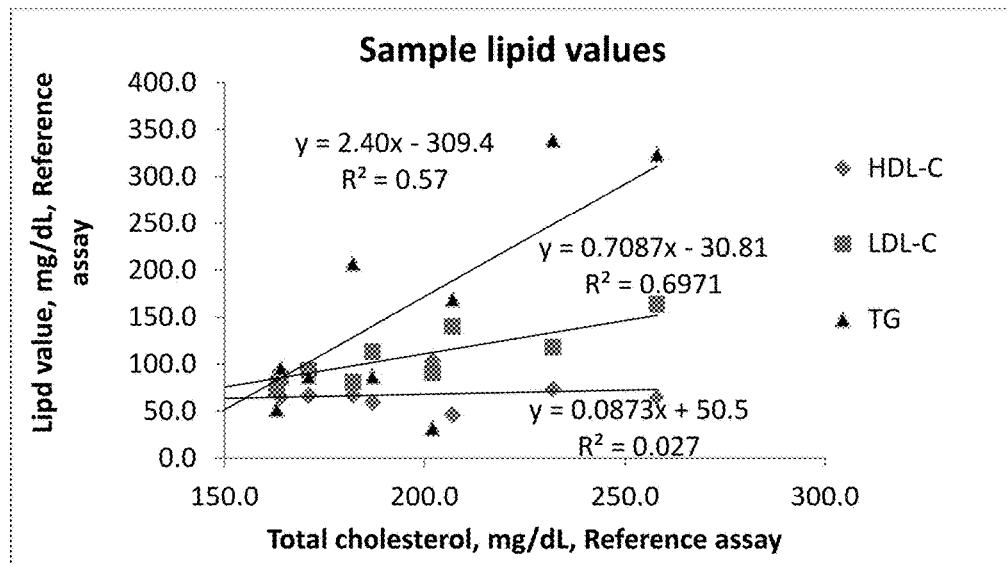
FIG. 2 plots sample lipid values found in lipoproteins, showing lipid value in units of milligrams per deciliter (mg/dL) along the vertical axis versus the total cholesterol (as mg/dL) along the horizontal axis, where the lipid value and the total cholesterol were measured using Advia® Chemistry Systems reagents and methods (Siemens Healthcare Diagnostics, Inc., Tarrytown, N.Y.).

Samples:

FIG. 2 shows the lipid content of lipoproteins as measured in the clinical serum samples (including results for triglycerides) used for the studies shown in the examples. As can be seen, there was poor to no correlation between the cholesterol in the various lipoprotein sub-forms. Also, the cholesterol levels spanned the range seen in normal subjects and those with lipemia and so provided a good test set for the methods of the invention. In the data below, samples were also analyzed by a reference method using the Advia® Chemistry System (Siemens Healthcare Diagnostics, Inc., Tarrytown, N.Y.).

Figure 3:
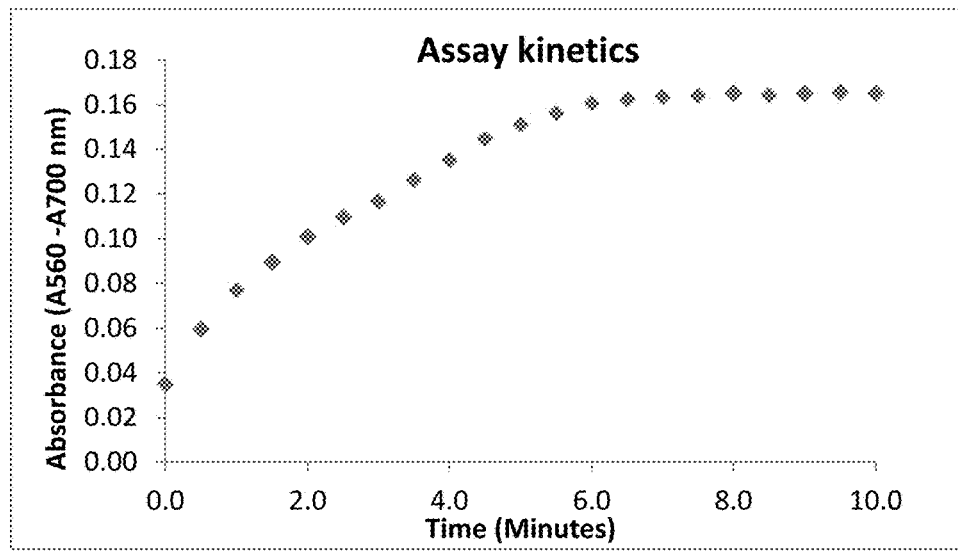
FIG. 3 plots assay kinetics for an exemplary experiment, where the difference in absorbance of light by a solution containing sample, reagent A and reagent B at a wavelength of 560 nanometers (nm) and at a wavelength of 700 nm ("Absorbance (A560-A700 mm)") was measured by spectrophotometry. Absorbance at a wavelength of 560 nm was determined by measuring the absorbance between 550 nm and 570 nm; absorbance at a wavelength of 700 nm was determined by measuring the absorbance between 690 nm and 710 nm. The time shown on the horizontal axis is time in minutes after the addition of Reagent B (the composition of Reagent B is described in Table 2).

Time Course of the Cholesterol Assay Reaction:

Color formation occurs in the present cholesterol assay method in several phases. Examples of such phased color formation is illustrated in the results obtained for a sample measured in an exemplary experiment, as presented in FIG. 3 (times refer to the time after adding reagent BC). The phases included:

1. A rapid phase (0 to about 2 minutes) when HDL-C and LDL-C were consumed.

2. A sigmoidal process corresponding to a slight "lag" followed by a rapid rise in color formation (about 2-about 6 minutes) when the remaining LDL-C were consumed.

3. A relatively slow consumption of VLDL-cholesterol (about 6-10 minutes or more) in a third phase.

Measurement of Lipoprotein Species by the Present Method and Correlations with Results of Reference Methods:

In some cases commercially available control materials were also measured. TC was measured using $\Delta A$ (560-700 nm) at ten minutes. LDL-C was measured by the difference in $\Delta A$ (560-700 nm) which occurred between two and six minutes. HDL-C was measured by $\Delta A_r$, the change in $\Delta A$ (560-700 nm) which occurred between zero and two minutes. ($\Delta A$ is the difference between the absorbance measured at 560 nm and the absorbance measured at 700 nm.) In the experiments of the present example, $\Delta A$ was measured by a M5 spectrophotometer (Molecular Devices, Sunnyvale, Calif.).

Measurements labeled "Reference assay" were made using the Siemens Advia® chemistry and methods (Siemens Healthcare Diagnostics, Inc.).

The following correlations were obtained which meet clinical assay requirements:

LDL-Cholesterol: For 15 samples and controls: y=0.989*x; $R^2$=0.978; x range: 7.7-230 mg/dL; x mean=118.1; Standard error of the estimate/Mean=6.8%

HDL-Cholesterol: For 10 samples: y=0.98*x+1.35; $R^2$=0.98; x range 40.3-103.4 mg/dL; x mean 67.2 mg/dL; Standard error of the estimate/Mean=4.0%

Total cholesterol: for 14 samples and controls: y=0.977*x; $R^2$=0.980; x range 15-304 mg/dL; x mean=195.6 mg/dL; Standard error of the estimate/Mean=4.3% (where * indicates multiplication).

Figure 4A:
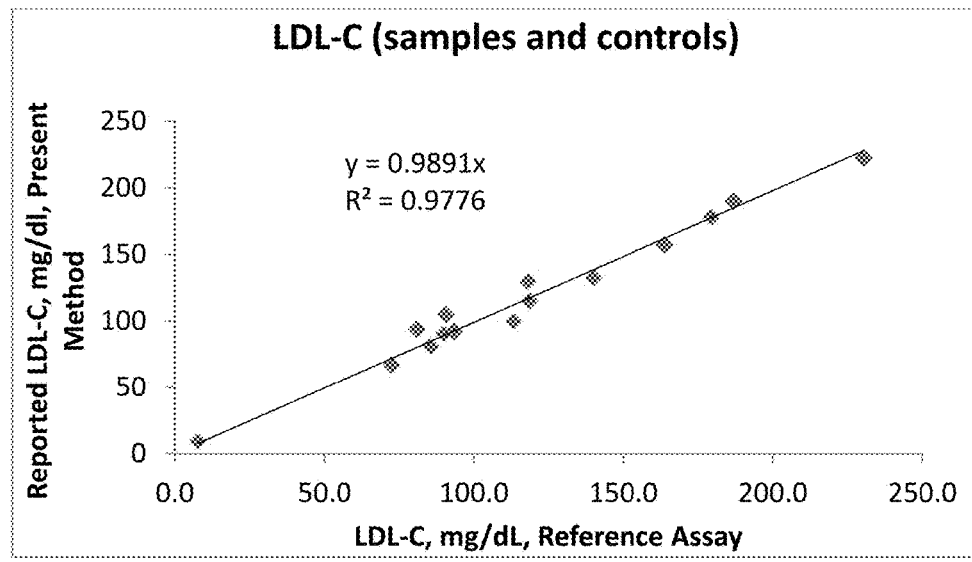
FIG. 4A shows LDL-C measurements using the kinetic data from a single, exemplary assay as disclosed herein, and plots the reported LDL-C, HDL-C, and TC values as determined by an assay as disclosed herein (where Reagent A is as described in Table 1 and Reagent B is as described in Table 2) along the vertical axis (in units of mg/dL) versus the LDL-C, HDL-C, and TC values (in mg/dL) determined by the dextran sulfate assay using the Siemens Direct assay. The initial point near (0,0) in FIG. 4A does not represent experimental data, but was included in the analysis and figures for clarity and to provide an anchor point for the fitted lines.
Figure 4B:
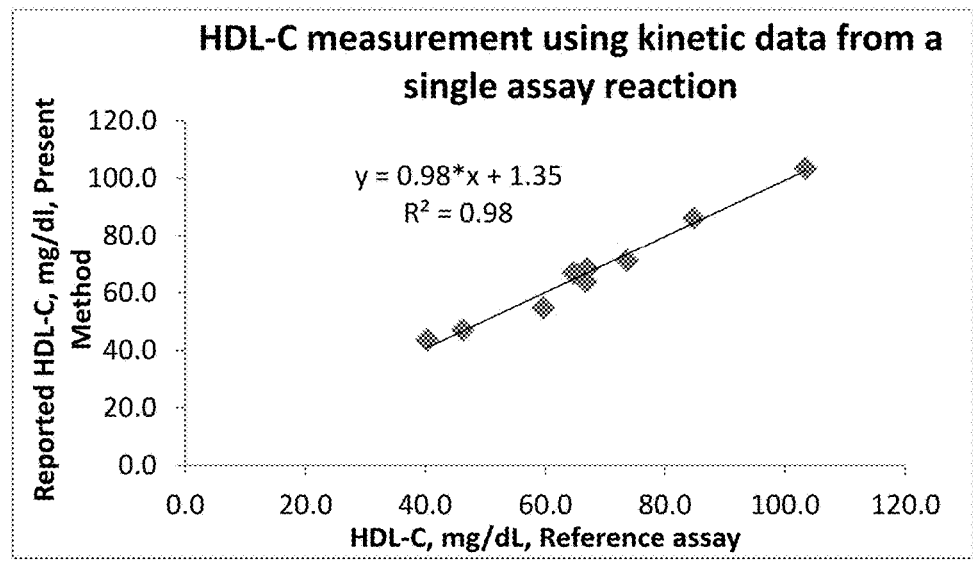
FIG. 4B shows HDL-C measurements using the kinetic data from a single, exemplary assay as disclosed herein, and plots the reported LDL-C, HDL-C, and TC values as determined by an assay as disclosed herein (where Reagent A is as described in Table 1 and Reagent B is as described in Table 2) along the vertical axis (in units of mg/dL) versus the LDL-C, HDL-C, and TC values (in mg/dL) determined by the dextran sulfate assay using the Siemens Direct assay.
Figure 4C:
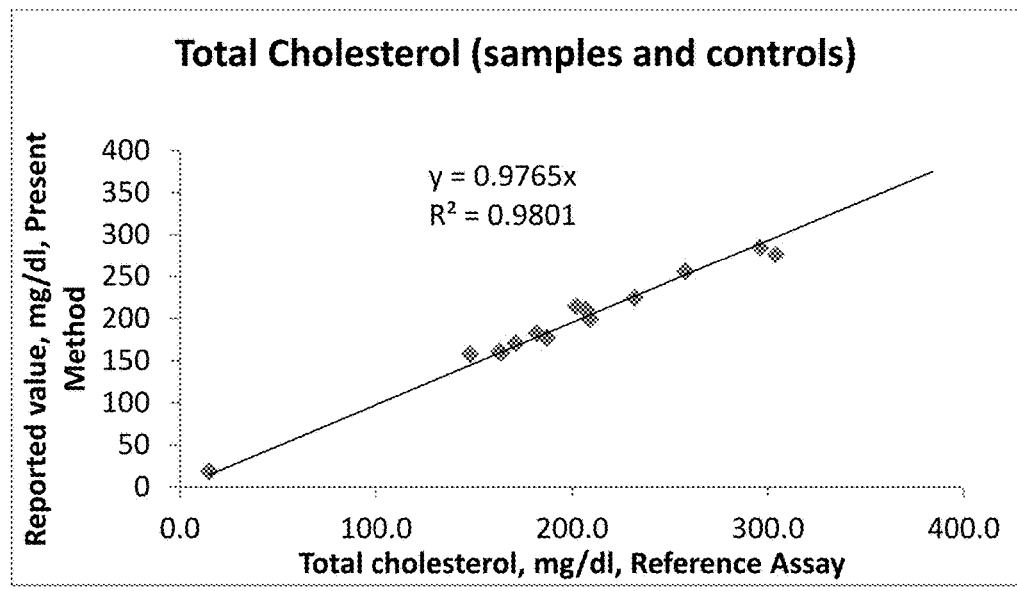
FIG. 4C shows TC measurements using the kinetic data from a single, exemplary assay as disclosed herein, and plots the reported LDL-C, HDL-C, and TC values as determined by an assay as disclosed herein (where Reagent A is as described in Table 1 and Reagent B is as described in Table 2) along the vertical axis (in units of mg/dL) versus the LDL-C, HDL-C, and TC values (in mg/dL) determined by the dextran sulfate assay using the Siemens Direct assay. The initial point near (0,0) in FIG. 4C does not represent experimental data, but was included in the analysis and figures for clarity and to provide an anchor point for the fitted lines.

These results from the present and reference methods are shown in graphic form in FIG. 4. The LDL-C results from the present and reference methods are shown in FIG. 4A in graphic form. The HDL-C results from the present and reference methods are shown in FIG. 4B in graphic form. The TC results from the present and reference methods are shown in FIG. 4C in graphic form.

The formula for calculating HDL-C was derived by using the estimate of the LDL-C from the same assay plus the rate measured between 0 and 2 minutes (where the * indicates multiplication):

HDL-Cholesterol=1.30−0.446*LDL-C+1255.5*($\Delta A$ (560-700 nm),2 min−($\Delta A$(560-700 nm),0 min)

The formula for calculating HDL-C was derived by using the estimate of the LDL-C from the same assay plus the rate measured between 0 and 2 minutes (where the * indicates multiplication):

HDL-Cholesterol=1.30−0.446*LDL-C+1255.5*($\Delta A$ (560-700 nm),2 min−($\Delta A$(560-700 nm),0 min)

Both factors (LDL-C and ($\Delta A$ (560-700 nm), 2 min−($\Delta A$ (560-700 nm), 0 min) were highly significantly correlated (p<0.0001).

The above equation was derived by multiple regression analysis of assay results presented herein using trial and error combinations of the measured absorbances, TC and LDL-C calculated from the absorbance data.

Conclusion: Use of specific reagent formulations and kinetic measurement of reaction product enable simultaneous measurement of total, LDL and HDL cholesterol.

Example 3 Triglyceride Assays

Figure 1B:
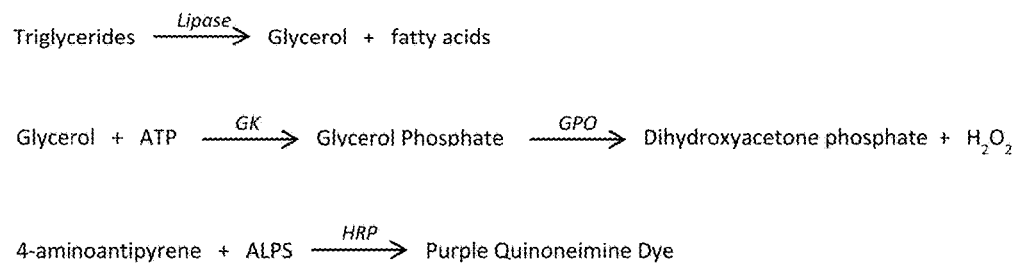
FIG. 1B shows an exemplary reaction scheme where triglycerides (e.g., as are found in a sample of blood) may react with a lipase to form glycerol and fatty acids. The glycerol may be phosphorylated, in the presence of adenosine triphosphate (ATP), by a glycerol kinase, and the resulting glycerol phosphate may be oxidized by glycerol-3-phosphate oxidase to provide dihydroxyacetone phosphate and hydrogen peroxide. Hydrogen peroxide, in the presence of horseradish peroxidase and colorants such as an aminoantipyrene (e.g., 4-aminoantipyrene) and an aniline-containing compound (e.g., N-Ethyl-N-(2-hydroxy-3-sulfopropyl)-3,5-dimethoxyaniline) to form a colored product (e.g., a quinoneimine dye, or Trinder dye, as indicated in the figure).

Triglyceride (TG) levels may be measured by an assay in which triglycerides in a sample are broken down into their constituent fatty acids and glycerol, and the glycerol levels measured photometrically as indicated in FIG. 1B. Glycerol may be phosphorylated by glycerol kinase in the presence of adenosine triphosphate (ATP), and the resulting glycerol phosphate oxidized by glycerol 3-phosphate oxidase to produce dihydroxyacetone phosphate and hydrogen peroxide. The hydrogen peroxide, with horseradish peroxidase (or other peroxidase) can react with colorants to produce a dye which can be measured by a spectrophotometer to determine the triglyceride content of the sample. Exemplary reagents Reagent AT and Reagent BT for use in this TG assay are shown in Table 4. As shown in the present example, 4-aminoantipyrene with N-Ethyl-N-(3-sulfopropyl) aniline will react with horseradish peroxidase in the presence of hydrogen peroxide to form a purple quineoneimine dye; the amount of dye formed can be determined by measuring absorbance at 560 nm, as indicated in the procedure below, and as shown in the experimental results reported in FIG. 5.

Triglyceride Assay Reagents

This assay uses an enzyme reaction cascade with results in the production of hydrogen peroxide ($H_2O_2$) which is used by Horseradish Peroxidase (HRP) to produce a purple color product. The reagents used in such assays include a Reagent AT and a Reagent BT. Examples of compositions suitable for such reagents are shown in Table 4A, and the compositions of particular specific exemplary Reagents AT and BT are shown in Table 4B.

TABLE 4A

Triglyceride Assay Reagents

| Reagent AT Components | Concentration Range |
|---|---|
| Adenosine-5'-triphosphate (ATP) salt (sodium, potassium, acetate, other salt) | 0.1 mM to 10 mM |
| Magnesium salt (e.g., chloride, sulfate, acetate, carbonate, or other salt) | 0.5 mM to 50 mM |
| Lipase (e.g., a bacterial lipase) | 1000 to 1,000,000 U/L |
| Surfactant (e.g., a Triton™, a TWEEN® or a Pluronic® surfactant) | 0.01% to 5% |
| Buffered saline (e.g., phosphate, HEPES, or MOPS buffered solution) | 1 to 300 mM |

| Reagent BT Components | Concentration |
|---|---|
| Peroxidase (e.g., from horseradish, HRP) | 150 U/L to 15,000 U/L |
| 4-aminoantipyrene (4-AA) | 0.1 mM to 10 mM |
| N-Ethyl-N-(3-sulfopropyl)aniline, sodium salt (ALPS) | 0.4 mM to 40 mM |
| Glycerol-3-Phosphate Oxidase (GPO) | 100 U/L to 20,000 U/L |
| Glycerokinase (GK) (e.g., from bacteria) | 5 U/L to 5000 U/L |
| Buffered saline (e.g., phosphate, HEPES, or MOPS buffered solution) | 1 mM to 300 mM |

Particular exemplary Reagents AT and BT may be made according to the ingredients and amounts as set out in Table 4B.

TABLE 4B

Triglyceride Assay Reagents

| | Concentration |
|---|---|
| Reagent AT Components | |
| Adenosine-5'-triphosphate (ATP) disodium salt | 1.5 mM |
| Magnesium Chloride (MgCl$_2$), anhydrous | 20 mM |
| Lipase from *Chromobacterium viscosum* | 400,000 U/L |
| Octyl Phenol Ethoxylate (e.g., Triton X-100 ®) | 0.3% |
| PBS with Tween 20 ® | Diluted to "1X" (~10 mM K$_x$PO$_4$, ~138 mM NaCl, ~2.7 mM KCl, ~0.05% Tween 20 ®) |
| Reagent BT Components | |
| Horseradish Peroxidase (HRP) | 5,000 U/L |
| 4-aminoantipyrene (4-AA) | 1 mM |
| N-Ethyl-N-(3-sulfopropyl)aniline, sodium salt (ALPS) | 4 mM |
| Glycerol 3-Phosphate Oxidase (GPO) from microorganism | 5,000 U/L |
| Glyerokinase (GK) from *Cellulomonas* sp. | 250 U/L |
| PBS with Tween20 ® | Diluted to "1X" (~10 mM K$_x$PO$_4$, ~138 mM NaCl, ~2.7 mM KCl, ~0.05% Tween 20 ®) |

Exemplary Assay Procedure for Triglycerides in Blood Serum of EDTA-Anticoagulated Plasma:

1. Samples (and/or calibrators) were diluted 1:30 with water.
2. Reagents and diluted samples were brought to 37° C. prior to the assay.
3. 20 µL, each of diluted sample, reagent AT and reagent BT as described in Table 4B were mixed in the wells of a 384-well microtiter plate.
4. The mixture of diluted sample, reagent AT and reagent BT as described in Table 4B were incubated at 37 C for 10 minutes.
5. Absorbance at 560 nm was read in a microtiterplate reader (Molecular Devices M5) following step 4.

Figure 5:
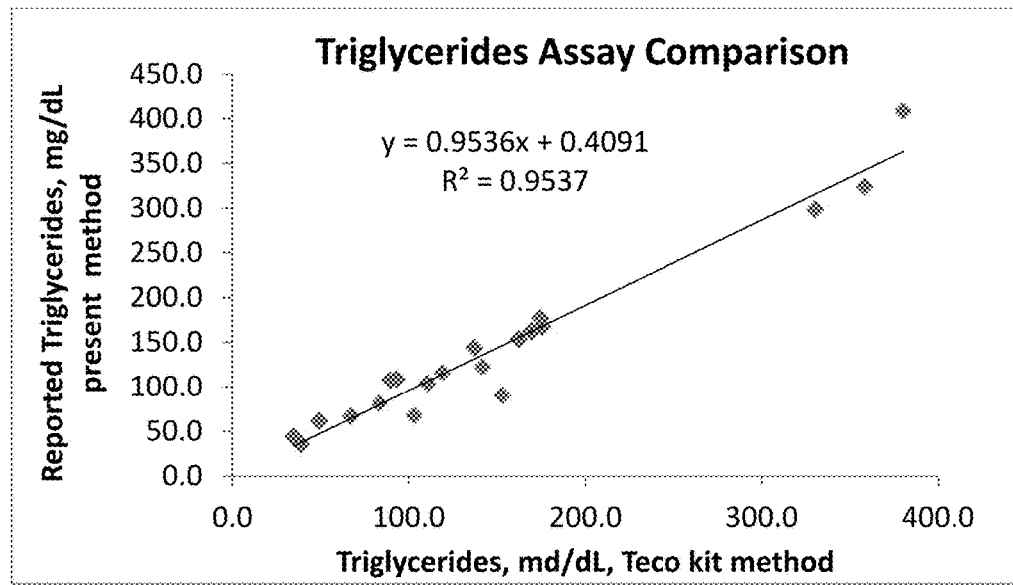
FIG. 5 shows the results of an exemplary triglyceride assay as described in Example 3, using Reagent AT and Reagent BT. Triglyceride levels obtained using the present novel methods are presented as the Y-axis value of each diamond in the figure, and are plotted versus triglyceride measurements made using a prior art method (the X-axis value for each diamond). The data have been fitted with a straight line having a slope near 1 (0.9536); the $R^2$ value of the least-squares fitting was 0.9537.

TG measurements made according to the above-described methods are shown in FIG. 5 (the measurements providing the position of the data points along the vertical axis); the data points are plotted versus TG measurements according to a prior art method (the method suggested by Teco Diagnostics, using the reagents of the commercially available Teco kit (Teco Diagnostics, Anaheim, Calif. 92807)). TG measured by the present methods agreed very closely with prior art TG measurements. If there had been perfect agreement between the prior art and present methods, the slope of the line drawn through these points would give a slope of 1. As shown in FIG. 5, the slope of the line drawn by linear regression through these points had a slope very near to one (slope=0.9536). Thus, the TG determination methods shown in this example correlate very well with those of other well-accepted methods.

Example 4 Combined Blood Cholesterol and Triglyceride Measurements

Measurements of cholesterol (C) and triglycerides (TG) may be made on aliquots of the same sample of blood, or on separate samples of blood taken from the same patient, in order to provide more complete clinical information than would be available from measurement of C alone or of TG alone. In addition, TG measurements can be used to provide a measure of the VLDL in the blood sample. Thus, measures of LDL-C, HDL-C, TC, VLDL-C, and TG may be obtained by the methods of Examples 1, 2, and 3, and estimating VLDL-C by the formula:

$$VLDL\text{-}C = TG/5.$$

TC may be measured directly according to the methods and assays disclosed herein; similarly, HDL-C and LDL-C may be measured directly according to the methods and assays disclosed herein. Since TC is a measure of the total of the cholesterol in a sample, TC is the sum of the cholesterol in the lipoprotein fractions in the sample, and so may be estimated by the relation TC=HDL-C+LDL-C+VLDL-C. Accordingly, by rearranging, a better determination of VLDL-C may be obtained from the measured amounts of HDL-C, LDL-C, and TC as follows:

$$VLDL\text{-}C = TC - HDL\text{-}C - LDL\text{-}C$$

and may be determined by according to the methods and formulas as described herein.

As discussed above, further methods for determining VLDL-C from the measured values of HDL-C, LDL-C, and TC, and from the measured values of TG, HDL-C, LDL-C, and TC, are disclosed herein. For example, in embodiments, the level of VLDL-C in a single sample, or a single portion of a sample, of blood of a subject may be calculated by the following relation:

$$VLDL\text{-}C = \alpha TC + \beta HDL\text{-}C + \gamma LDL\text{-}C + \delta TG + a_1(TG+\varepsilon)(TC+\kappa) + \lambda$$

where $\alpha$, $\beta$, $\gamma$, $\delta$, and $a_1$ are constants which multiply TC, HDL-C, LDL-C, TG, and the cross-term (TG+$\varepsilon$)(TC+$\kappa$) respectively (in a cross-term, the terms in one parenthesis multiply the terms in the other parenthesis); and where $\varepsilon$, $\kappa$, and $\lambda$ are additive constants to be added to TG, TC, and the sum of all other factors, respectively. In a particular embodiment, where $\gamma=0$, the level of VLDL-C in a single sample, or a single portion of a sample, of blood of a subject may be calculated from these measurements, for example, by the relation:

$$VLDL\text{-}C = \alpha TC + \beta HDL\text{-}C + \delta TG + a_1(TG+\varepsilon)(TC+\kappa) + \lambda$$

where $\alpha$, $\beta$, $\delta$, and $a_1$ are constants which multiply TC, HDL-C, TG, and (TG+$\varepsilon$)(TC+$\kappa$), respectively; and where $\varepsilon$, $\kappa$, and $\lambda$ are additive constants to be added to TG, TC, and the sum of all other factors, respectively.

An example of such a calculation of VLDL-C is shown in FIG. 6, where 20 values of VLDL-C determined by the equation above based on measurements as disclosed herein (plotted along the y-axis) are plotted versus corresponding VLDL-C measurements made by prior art ultracentrifugation methods (plotted along the x-axis). As shown in FIG. 6, the VLDL-C values calculated according to the formula above quite accurately track those obtained by prior art methods. In the plot shown in FIG. 6, $\lambda$ ("intercept") has a value of −2.62; $\alpha$ has a value of 0.15; $\beta$ has a value of −0.55; $\delta$ has a value of 0.15; $a_1$ has a value of 0.0015; $\varepsilon$ has a value of −192; and $\kappa$ has a value of −188. The VLDL-C values calculated by the equation above agree very well with the VLDL-C values obtained by ultracentrifugation methods (R squared 0.959). The best fit line shown in the figure was calculated using JMP software (SAS institute, Inc., Cary N.C., 27513), and analysis of variance for this model and these parameters had an F ratio of 93.4 indicating that such a good fit would be found by chance with a probability of less than 0.001, a highly significant result.

While the above is a description of the embodiment as described herein, it is possible to use various alternatives, modifications and equivalents. It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2012 Theranos, Inc.

The invention claimed is:

1. A reagent for use in a cholesterol assay, said reagent comprising a lipoprotein solubilization agent, lipoprotein interactant, and a buffer, wherein said lipoprotein interactant is present at a concentration level that provides for conversion of high density lipoprotein cholesterol (HDL-C) to a measureable colored product at a substantially different rate than for conversion of low density lipoprotein cholesterol (LDL-C) to a measureable colored product and at a substantially different rate than for conversion of very low density lipoprotein cholesterol (VLDL-C) to a measureable colored product when said reagent is used in a cholesterol assay;
   wherein the lipoprotein interactant comprises a negatively charged polysaccharide and a divalent cation, or a salt thereof, in a ratio of between 0.003 to 0.007.

2. The reagent of claim 1, comprising α-cyclodextrin sulfate, dextran sulfate, magnesium chloride, 4-aminoantipyrene and a sodium phosphate buffer.

3. The reagent of claim 2, wherein said ratio of dextran sulfate to magnesium ions is between about 0.003 to about 0.005.

4. The reagent of claim 1, said reagent comprising magnesium and dextran sulfate in a ratio of dextran sulfate to magnesium ions effective that there is no substantial precipitation of low-density lipoprotein (LDL), or that there is no substantial precipitation of very low-density lipoprotein (VLDL), or both, when a blood sample containing LDL or VLDL is put in contact with said reagent.

5. The reagent of claim 4, wherein said ratio of dextran sulfate to magnesium ions is between about 0.003 to about 0.005.

6. The reagent of claim 1, wherein said lipoprotein solubilization agent is selected from a surfactant, or a negatively charged α-cyclodextrin derivative; and said lipoprotein interactant comprises a low molecular weight negatively charged dextran derivative.

7. The reagent of claim 6, wherein said ratio of dextran sulfate to magnesium ions is between about 0.003 to about 0.005.

8. The reagent of claim 1, wherein said lipoprotein solubilization agent is a nonionic surfactant or a zwitterionic surfactant.

9. The reagent of claim 1, wherein said lipoprotein interactant is a dextran derivative.

10. A kit comprising a reagent and instructions for the use of said reagent in a cholesterol assay, the reagent comprising α-cyclodextrin sulfate, dextran sulfate, magnesium chloride, 4-aminoantipyrene and a sodium phosphate buffer, wherein the ratio of dextran sulfate to magnesium ions in the reagent is between about 0.003 to about 0.007.

* * * * *